US006693105B1

(12) United States Patent
Underiner et al.

(10) Patent No.: US 6,693,105 B1
(45) Date of Patent: Feb. 17, 2004

(54) HYDROXYL-CONTAINING COMPOUNDS

(75) Inventors: Gail E. Underiner, Malvern, PA (US); David Porubek, Seattle, WA (US); J. Peter Klein, Vashon, WA (US); Paul Woodson, Edmonds, WA (US); Stephen J. Klaus, Seattle, WA (US); Anil M. Kumar, Mercer Island, WA (US); John Tulinsky, Seattle, WA (US)

(73) Assignee: Cell Therapeutics, Inc., Seattle, WA (US)

(*) Notice: Subject to any disclaimer, the term of this patent is extended or adjusted under 35 U.S.C. 154(b) by 0 days.

(21) Appl. No.: 09/361,145

(22) Filed: Jul. 27, 1999

Related U.S. Application Data

(63) Continuation-in-part of application No. 09/288,556, filed on Apr. 9, 1999, and a continuation-in-part of application No. 08/756,703, filed on Nov. 26, 1996, now Pat. No. 6,133,274, which is a continuation of application No. 08/153,356, filed on Nov. 16, 1993, which is a continuation-in-part of application No. 07/976,353, filed on Nov. 16, 1992, now Pat. No. 5,473,070, said application No. 09/288,556, is a continuation-in-part of application No. 09/008,020, filed on Jan. 16, 1998.

(51) Int. Cl.[7] .................. A61K 31/522; C07D 473/00; G01N 33/00
(52) U.S. Cl. ................. 514/263.3; 514/263.2; 544/267; 436/98
(58) Field of Search .............. 514/263.2, 263.3; 544/267; 436/98

(56) References Cited

U.S. PATENT DOCUMENTS

| | | | |
|---|---|---|---|
| 3,422,107 A | 1/1969 | Mohler et al. | 544/271 |
| 3,737,433 A | 6/1973 | Mohler et al. | 544/271 |
| 4,515,795 A | 5/1985 | Hinze et al. | 544/267 |
| 4,576,947 A | 3/1986 | Hinze et al. | 544/267 |
| 4,599,414 A | 7/1986 | Sugimoto et al. | 544/269 |
| 4,612,315 A | 9/1986 | Jacobson et al. | 544/269 |
| 4,636,507 A | 1/1987 | Kreutzer et al. | 514/263 |
| 4,833,146 A | 5/1989 | Gebert et al. | 514/263 |
| 4,845,102 A | 7/1989 | Sakurai et al. | 514/263 |
| 4,965,271 A | 10/1990 | Mandell et al. | 514/263 |
| 5,039,666 A | 8/1991 | Novick et al. | 514/37 |
| 5,068,236 A | 11/1991 | Suzuki et al. | 544/267 |
| 5,096,906 A | 3/1992 | Mandell et al. | 514/263 |
| 5,118,500 A | 6/1992 | Händel et al. | 544/267 |
| 5,473,070 A | * 12/1995 | Underiner et al. | 514/263 |
| 5,612,349 A | * 3/1997 | Bianco et al. | 514/263 |
| 5,629,423 A | 5/1997 | Klein et al. | 514/258 |
| 5,648,357 A | 7/1997 | Bianco et al. | 514/263 |
| 5,734,051 A | 3/1998 | Spicer et al. | |

FOREIGN PATENT DOCUMENTS

WO 94/22449 * 10/1994

OTHER PUBLICATIONS

Bianco et al., "Pentoxifylline (PTX) and GM–CSF Decrease Tumor Necrosis Factor–ALPHA (TNF–α) Levels in Patients Undergoing Allogeneic Bone Marrow Transplantation (BMT)", Blood, 76:Supplement 1 (522), p. 133a, 1991.
Bianco et al., "Phase I–II Trial of Pentoxifylline for Prevention of Transplant–Related Toxicities Following Bone Marrow Transplantation", Blood, 78:1205, 1991.
Davis et al., "Microbial Models of Mammalian Metabolism: Microbial Reduction and Oxidation of Pentoxifylline", Applied Environment Microbiol., 48:2, pp. 327–331, Aug. 1984.
Singer et al., "Effect of Methoylxanthine Derivatives on T Cell Activation", Bone Marrow Transplantation, 10:19, pp. 19–25, 1992.
Kanehira et al., Chem. Abstr., vol. 110, 212848X (1989).
"Development of $T_H$ 1 CD4[+] T Cells Through IL–12 Produced by Listeria–Induced Macrophages", by Hsieh et al., Science, vol. 260, Apr. 23, 1993, pp. 547–549.
"Natural Killer Cell Stimulatory Factor (Interleukin 12 [IL–12]) Induces T Helper Type 1 (Th1)–specific Immune Responses and Inhibits the Development of IL–4–producing Th Cells", by Manetti et al., Journal of Exp. Medicine, vol. 177, Apr. 1993, pp. 1199–1204.

(List continued on next page.)

Primary Examiner—Richard L. Raymond
Assistant Examiner—Tamthom N. Truong
(74) Attorney, Agent, or Firm—McDermott, Will & Emery

(57) ABSTRACT

Disclosed are therapeutic compounds having the formula:

$$(R)_j\text{—(CORE MOIETY)},$$

including resolved enantiomers, diastereomers, hydrates, salts, solvates or mixtures thereof where j is an integer from one to three. The core moiety is a bicyclic ring structure having at least one heterocyclic ring that contains five to six ring atoms and up to two nitrogen heteroatoms. R is selected from the group consisting of hydrogen, halogen, hydroxyl, amino, substituted or unsubstituted benzyl, $C_{1-6}$ alkyl or $C_{1-6}$ alkenyl, and at least one R has the formula I:

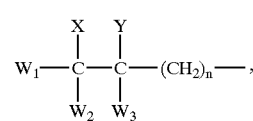

n is an integer from 1 to 20, at least one of X or Y is —OH. Another of X or Y, which is not —OH, is hydrogen, $CH_3$—, $CH_3$—$CH_2$—, $CH_3$—$(CH_2)_2$—or $(CH_3)_2$—$CH_2$—, and each $W_1$, $W_2$, and $W_3$ is independently hydrogen, $CH_3$—, $CH_3$—$CH_2$—, $CH_3$—$(CH_2)_2$— or $(CH_3)_2$—$CH_2$—. The X, Y, $W_1$, $W_2$, or $W_3$ alkyl groups may be unsubstituted or substituted by an hydroxyl, halo or dimethylamino group. The disclosed compounds and therapeutic compositions thereof are useful in treating individuals having a disease or treatment-induced toxicity, mediated by second messenger activity.

18 Claims, 10 Drawing Sheets

OTHER PUBLICATIONS

"Identification and Purification of Natural Killer Cell Stimulatory Factor (NKSF), A Cytokine with Multiple Biologic Effects on Human Lymphocytes", by Kobayashi et al., Journal of Exp. Medicine, vol. 170, Sep. 1989, pp. 827–846.

"Interleukin 12: A Key Modulator of Immune Function", by Wolf et al., Stem Cells, vol. 12, 1994, pp. 154–168.

"Internleukin–12: A Proinflammatory Cytokine with Immunoregulatory Functions that Bridge Innate Resistance and Antigen–Specific Adaptive Immunity", by Trinchieri, Annu. Rev. Immunol., vol. 13, 1995, pp. 251–276.

"The Role of Cytokines in Various Animal Models of Inflammation", by Heremans et al., Lymphokine Research, vol. 8, No. 3, 1989, pp. 329–333.

"Inducible Cell Contact Signals Regulate Early Activation Gene Expression During B–T Lymphocyte Collaboration", by Klaus et al., The Journal of Immunology, vol. 49, No. 6, Sep. 1992, pp. 1867–1875.

"Generation of Interleukin 4 (IL–4)–producing Cells In Vivo and In Vitro: IL–2 and IL–4 Required for In Vitro Generation of IL–4–producing Cells", by Le Gros, et al., The Journal of Experimental Medicine, vol. 172, Sep. 1990, pp. 921–929.

"Inhibition of Human Interleukin–12 Production by Pentoxifylline", by Moller et al., Immunology, vol. 91, 1997, pp. 197–203.

"The Immunology of Multiple Sclerosis and its Animal Model, Experimental Allergic Encephalomyelitis", by Owens et al., Neurologic Clinics, vol. 13, No. 1, Feb. 1995.

"Interleukin 12", R& D Systems Catalog, pp. 67–69, 1995.

"Long–term Treatment of Chronic Relapsing Experimental Allergic Encephalomyelitis by Transforming Growth Factor–$\beta$2", by Racke et al., Journal of Neuroimmunology, vol. 46, 1993, pp. 175–184.

"Phosphodiesterase Inhibitor Pentoxifylline, a Selective Suppressor of T Helper Type 1– but not Type 2–associated Lymphokine Production, Prevents Induction of Experimental Autoimmune Encephalomyelitis in Lewis Rats", by Rott et al., Eur. J. Immumol., vol. 23, 1993, pp. 1745–1751.

"The Role of IL–12 in the Induction of Organ–Specific Autoimmune Diseases", by Trembleau et al., Immunology Today, vol. 16, No. 8, 1995, pp. 383–386.

Remington Pharmaceutical Sciences, Chapters 83–92, 1990, pp. 1519–1751.

* cited by examiner

HYDROXYL-CONTAINING COMPOUNDS

CROSS REFERENCE TO RELATED APPLICATIONS

This application is a continuation-in-part of U.S. application Ser. No. 08/756,703, filed Nov. 26, 1996 now U.S. Pat. No. 6,133,274, and U.S. application Ser. No. 09/288, 556, filed Apr. 9, 1999. U.S. application Ser. No. 08/756,703 is a continuation of U.S. application Ser. No. 08/153,356, filed Nov. 16, 1993, which is a continuation-in-part of U.S. application Ser. No. 07/976,353, filed Nov. 16, 1992, now U.S. Pat. No. 5,473,070. U.S. application Ser. No. 09/288, 556 is a continuation-in-part of U.S. application Ser. No. 09/008,020, which was filed Jan. 16, 1998. The disclosures of the aforementioned applications are incorporated by reference herein in their entirety.

TECHNICAL FIELD OF THE INVENTION

The invention provides a class of substituted hydroxyl-containing compounds for use in inhibiting specific intracellular signaling events often induced by noxious or inflammatory stimuli. More specifically, the inventive compounds have at least one hydroxyl-containing substituent bonded to a core moiety. The inventive compounds are useful antagonists to control intracellular levels of specific non-arachidonyl sn-2 unsaturated phosphatidic acids and corresponding phosphatidic acid-derived diacylglycerols which occur in response to cellular proliferative stimuli.

BACKGROUND ART

Pentoxifylline (1-(5-oxohexyl)-3,7-dimethylxanthine), abbreviated PTX and disclosed in U.S. Pat. Nos. 3,422,307 and 3,737,433, is a xanthine derivative which has seen widespread medical use for the increase of blood flow. Metabolites of PTX were summarized in Davis et al., *Applied Environment Microbial.* 48:327, 1984. One such metabolite, 1-(5-hydroxyhexyl)-3,7-dimethylxanthine, designated M1 and disclosed in U.S. Pat. Nos. 4,515,795 and 4,576,947, increases cerebral blood flow. In addition, U.S. Pat. Nos. 4,833,146 and 5,039,666 disclose use of tertiary alcohol analogs of xanthine for enhancing cerebral blood flow.

U.S. Pat. No. 4,636,507 discloses that PTX and M1 stimulate chemotaxis in polymorphonuclear leukocytes in response to a chemotaxis stimulator. PTX and related tertiary alcohol substituted xanthines inhibit activity of certain cytokines to affect chemotaxis (U.S. Pat. Nos. 4,965,271 and 5,096,906). Administration of PTX and GM-CSF decrease tumor necrosis factor (TNF) levels in patients undergoing allogeneic bone marrow transplant (Bianco et al., *Blood* 76: Supplement 1 (522A), 1990). Reduction in bone marrow transplant-related complications accompanied reduction in assayable levels of TNF. However, in normal volunteers, TNF levels were higher among PTX recipients. Therefore, elevated levels of TNF are not the primary cause of such complications.

Therefore, effective therapeutic compounds that are safe and effective for human or animal administration and that can maintain cellular homeostasis in the face of a variety of inflammatory stimuli are needed. The invention is a result of research conducted in looking for such compounds.

SUMMARY OF THE INVENTION

We have found a genus of compounds useful in a large variety of therapeutic indications for treating or preventing disease mediated by intracellular signaling through one or two specific intracellular signaling pathways. In addition, the inventive compounds and pharmaceutical compositions are suitable for normal routes of therapeutic administration (e.g., parenteral, oral, topical, etc.) for providing effective dosages.

In one of its aspects, the invention includes a method for treating an individual having a disease or treatment-induced toxicity that is characterized by, or can be treated by inhibiting, an immune response or a cellular response to external or in situ primary stimuli, the cellular response being mediated through a specific phospholipid-based second messenger described herein. The second messenger pathway is activated in response to various noxious, proinflammatory or proliferative stimuli characteristic of a variety of disease states. More specifically, the invention includes methods for treating or preventing clinical symptoms of various disease states or reducing toxicity of other treatments by inhibiting cellular signaling through a second messenger pathway involving signaling through a non-arachidonyl phosphatidic acid intermediate. Treatment is carried out by administering an inventive compound, and pharmaceutical compositions thereof, having the formula:

$(R)_j$—(CORE MOIETY), including resolved enantiomers and/or diastereomers, hydrates, salts, solvates and mixtures thereof, wherein j is an integer from one to three, the core moiety comprises a bicyclic ring structure having at least one heterocyclic ring that contains five to six ring atoms and up to two nitrogen heteroatoms, R is selected from the group consisting of hydrogen, halogen, hydroxyl, amino, substituted or unsubstituted benzyl, $C_{1-6}$ alkyl or $C_{1-6}$ alkenyl, preferably the alkyl or alkenyl groups being substituted by an hydroxy, halogen and dimethylamine and/or interrupted by an oxygen atom. Preferred R include, but are not limited to, methyl, ethyl, isopropyl, n-propyl, isobutyl, n-butyl, t-butyl, 2-hydroxyethyl, 3-hydroxypropyl, 3-hydroxy-n-butyl, 2-methoxyethyl, 4-methoxy-n-butyl, 5-hydroxyhexyl, 2-bromopropyl, 3-dimethylaminobutyl, 4-chloropentyl, and the like. Particularly preferred R are ethyl, methyl, or H, and most preferably, methyl or H. At least one R has the formula I:

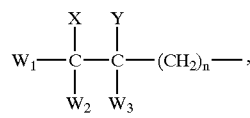

wherein n is an integer from 1 to 20, preferably an integer from 3 to 15, more preferably from 6 to 12, and at least one of X or Y is —OH. If only one of X or Y is —OH, then the other X or Y is hydrogen, $CH_3$—, $CH_3$—$CH_2$—, $CH_3$—$(CH_2)_2$—, or $(CH_3)_2$—$CH_2$—, and $W_1$, $W_2$, and $W_3$ are independently hydrogen, $CH_3$—, $CH_3$—$CH_2$—, $CH_3$—$(CH_2)_2$—, or $(CH_3)_2$—$CH_2$—, wherein X, Y, $W_1$, $W_2$, and $W_3$ alkyl groups may be substituted by an hydroxyl, halo or dimethylamino group and/or interrupted by an oxygen atom, hydrogen or alkyl ($C_{1-4}$). Especially preferred compounds have X and Y both being —OH and each of $W_1$, $W_2$, and $W_3$ being hydrogen or methyl. Preferably R having formula I structure is bonded to a ring nitrogen.

Exemplary bicyclic core moieties include, without limitation, substituted or unsubstituted: xanthinyl, dioxotetrahydropteridine, phthalimide, homophthalimide, benzoyleneurea and quinazoline-4(3H)-one. In one preferred embodiment, the core moiety is xanthine or a xanthine derivative.

Especially preferred xanthine compounds have the following formula II:

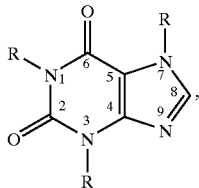

wherein R is selected from the foregoing members. Most preferably, a single R having formula I above is bonded to the $N_1$ xanthine nitrogen in formula II or each of two formula I R are bonded to $N_1$ and $N_7$ xanthine nitrogens, respectively. Remaining R substituents are preferably selected from the group consisting of hydrogen, methyl, fluoro, chloro and amino.

The compounds of the present invention are typically used as pharmaceutical compositions combined with a pharmaceutically acceptable excipient. The pharmaceutical composition may be formulated for oral, parenteral, ocular or topical administration to a patient.

In one of its aspects, the invention provides a method for modulating the response of a target cell to a stimulus by contacting the target cell with an effective amount of a compound of the invention. The stimulus is capable of elevating the cellular level of non-arachidonate phosphatidic acid (PA) and diacylglycerol(DAG) derived therefrom, and the compound is provided in an amount that is effective to reduce these elevated levels by an amount that is equal to or greater than that produced by treating the cells with 0.5 mmol pentoxifylline (PTX).

In another of its aspects, the invention provides a method for treating an individual having a disease or treatment-induced toxicity, mediated through a specific phospholipid-based second messenger, by administering a pharmaceutically effective amount of a compound of the invention. The disease is characterized by or can be treated by inhibiting an immune response or cellular response to external or in situ primary stimuli.

The disease or treatment-induced toxicity is selected from the group consisting of: tumor progression involving tumor stimulation of blood supply (angiogenesis) by production of fibroblast growth factor (FGF), vascular endothelial growth factor (VEGF) or platelet-derived growth factor (PDGF); tumor invasion and formation of metastases through adhesion molecule binding, expressed by vascular endothelial cells (VCAM and ICAM); tissue invasion through tumor metalloprotease production such as MMP-9; autoimmune diseases caused by dysregulation of the T cell or B cell immune systems, treatable by suppression of the T cell or B cell responses; acute allergic reactions including, but not limited to, asthma and chronic inflammatory diseases, mediated by pro-inflammatory cytokines including tumor necrosis factor (TNF) and IL-1, and rheumatoid arthritis, osteoarthritis, multiple sclerosis or insulin dependent diabetes mellitus (IDDM), associated with enhanced localization of inflammatory cells and release of inflammatory cytokines and metalloproteases; smooth muscle cell, endothelial cell, fibroblast and other cell type proliferation in response to growth factors, such as PDGF-AA, BB, FGF, EGF, etc. (i.e., atherosclerosis, restenosis, stroke, and coronary artery disease); activation of human immunodeficiency virus infection (AIDS and AIDS related complex); HIV-associated dementia; kidney mesengial cell proliferation in response to IL-1, MIP-1α, PDGF or FGF; inflammation; kidney glomerular or tubular toxicity in response to cyclosporin A or amphotericin B treatment; organ toxicity (e.g., gastrointestinal or pulmonary epithelial) in response to a cytotoxic therapy (e.g., cytotoxic drug or radiation); effects of non-alkylating anti-tumor agents; inflammation in response to inflammatory stimuli (e.g., TNF, IL-1 and the like) characterized by production of metalloproteases or allergies due to degranulation of mast cells and basophils in response to IgE or RANTES; bone diseases caused by overproduction of osteoclast-activating factor (OAF) by osteoclasts; CNS diseases resulting from over-stimulation by proinflammatory neurotransmitters such as, acetylcholine, serotonin, leuenkephalin or glutamate; acute inflammatory diseases such as septic shock, adult respiratory distress syndrome; multi-organ dysfunction associated with inflammatory cytokine cascade; and combinations thereof.

In many cell types, signaling is dependent upon generation of a broad variety of non-arachidonyl PA species, some of which are generated from lyso-PA by the enzyme lyso-PA acyl transferase (LPAAT). Generation of each of these PA species (the predominant forms being: 1-acyl and 1-alkyl 2-linoleoyl PA compounds, generated by LPAAT) serves to effect both proliferative and/or inflammatory signaling in the diseases discussed and cell systems described above.

In yet another aspect, the invention provides a method for treating or preventing acute and chronic inflammatory diseases, AIDS and AIDS related complex, alcoholic hepatitis, allergies due to degranulation of mast cells and basophils, angiogenesis, asthma, atherosclerosis, autoimmune thyroiditis, coronary artery disease, glomerula nephritis, hairloss or baldness, HIV-associated dementia, inflammatory bowel disease, insulin dependent diabetes mellitus, lupus, malignancies, multiple sclerosis, myelogenous leukemia, organ or hematopoietic in response to cytotoxic therapy, osteoarthritis, osteoporosis, peridontal disease, premature labor secondary to uterine infection, psoriasis, restenosis, rheumatoid arthritis, sleep disorders, septic shock, sepsis syndrome, scleroderma, stroke and transplant rejection in a mammal in need of such treatment, comprising administering a pharmaceutically effective amount of a compound of the invention or a pharmaceutical composition thereof.

In yet another aspect, the invention provides a method for inhibiting a cellular process or activity mediated by IL-12 signalling comprising contacting IL-12 responsive cells with an inventive compound, preferably a compound of the invention having a xanthinyl core moiety, and determining that the response of the target cell is thereby modulated.

In still yet another aspect, the present invention provides a method for treating a Th1 cell-mediated inflammatory response in a mammal in need of such treatment, the method comprising administering to the mammal a therapeutically effective amount of an inventive compound having the ability to inhibit an IL-12 mediated cellular process or activity, thereby inhibiting the inflammatory response. The inflammatory response is associated with a disease or condition selected from the group consisting of chronic inflammatory disease, chronic intestinal inflammation, arthritis, psoriasis, asthma and autoimmune disorders (e.g., type-1 IDDM, multiple sclerosis, rheumatoid arthritis, uveitis, inflammatory bowel disease, lupus disorders, and acute and chronic graft-versus-host disease).

The inventive compounds are of particular significance for inhibiting IL-2-induced proliferative responses. IL-2 signaling inhibition is potentially useful in the treatment of numerous disease states involving T-cell activation and hyperproliferation. Exemplary autoimmune diseases are lupus, scleroderma, rheumatoid arthritis, multiple sclerosis, glomerula nephritis, insulin dependent diabetes mellitus (IDDM), as well as potential malignancies, including but not limited to, chronic myelogenous leukemia as well as others.

DETAILED DESCRIPTION OF THE INVENTION

Figure 1:
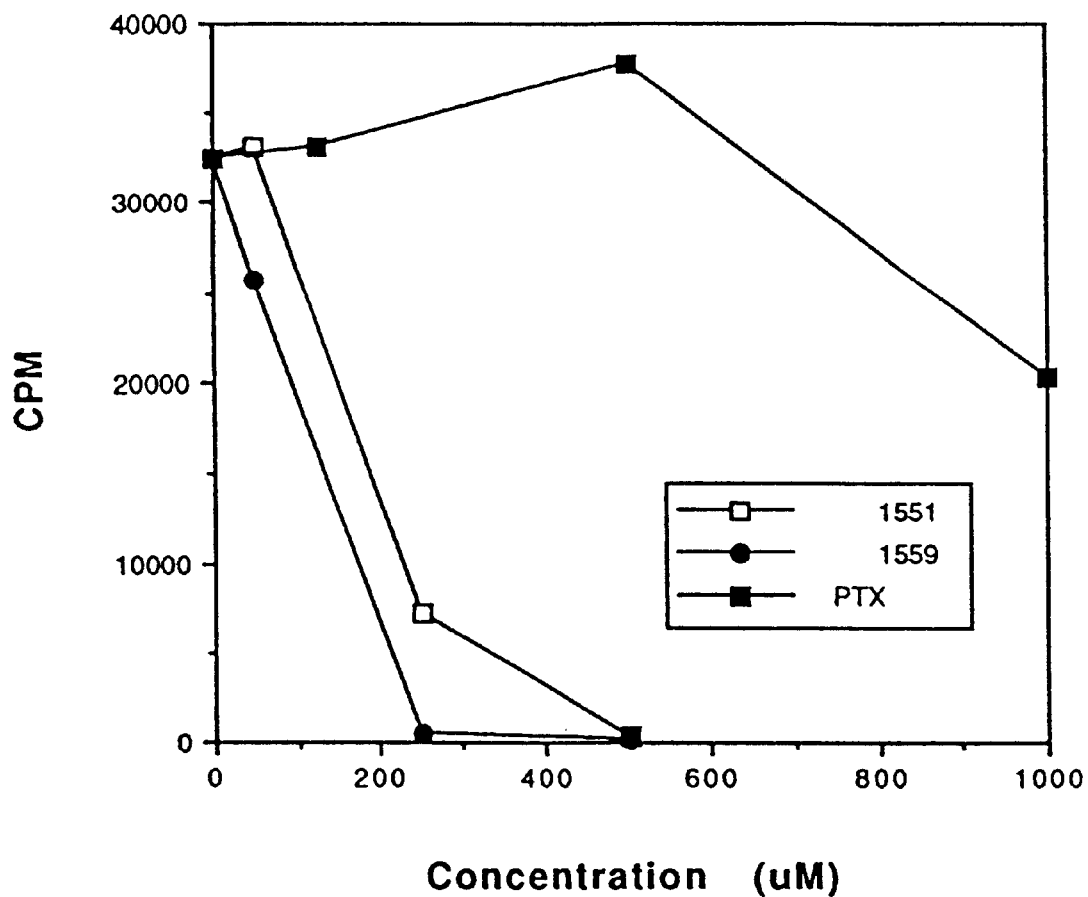
FIG. 1 shows a mixed lymphocyte reaction of PTX and two inventive compound nos. 1551 and 1559 (chemical names and structures below). The mixed lymphocyte reaction shows a proliferative response of PBMC (peripheral blood mononuclear cells) to allogeneic stimulation determined in a two-way mixed lymphocyte reaction. Each of the inventive compounds tested was more effective and more potent than PTX in this immune modulating activity assay procedure.

The invention provides a genus of compounds which can control cellular behavior by a particular phase of a secondary messenger pathway system (Bursten et al., *J. Biol. Chem.* 266:20732, 1991). The second messengers are lipids or phospholipids and use the following abbreviations:

PE=phosphatidyl ethanolamine

LPE=lysophosphoethanolamine
PA=phosphatidic acid
LPA=lysophosphatidic acid
DAG=diacylglycerol
LPLD=lysophospholipase-D
LPAAT=lysophosphatidic acid acyl transferase
PAPH=phosphatidic acid phosphohydrolase
PLA2=phospholipase A-2.
PLD=phospholipase D
PAA=phosphoarachidonic acid
PLA-2=phospholipase A2
PC=phosphatidyl choline "remodeled" PA, cyclic pathway=PAA, LPA, PA and DAG intermediates substituted with 1-saturated, 2-linoleoyl or 1,2-dioleoyl, dioleoyl/1,2-sn-dilinoleoyl at the indicated sn-1 and sn-2 positions.

"Classical PI Pathway"=PI, DAG, PA intermediates substituted with 1-stearoyl, 2-arachidonoyl fatty acyl side chains.

"PLD-generated PA"=PE, PC, LPA, PA and DAG intermediates substituted with, e.g. 1,2-sn-dioleoyl-, 1-alkyl, 2-linoleoyl-, and 1-alkyl, 2-docosahexaenoyl- side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as IL-1, IL-2 or TNF) acting at a receptor on a cellular surface. An immediate detectable effect is an elevation of levels of PA and DAG. Administration of the compounds of the invention reverse this elevation.

The compounds and pharmaceutical compositions of the invention include inhibitors of subspecies of LPAAT and PAPH enzymes with substrate specificity for intermediates with 1,2-diunsaturated and 1-alkyl, 2-unsaturated subspecies. One representative example of such an inhibitor (although not within the genus of inventive compounds) is PTX. PTX blocks PAPH in a specific activation pathway that does not involve PI but rather derives from a PA that is largely composed of 1,2-diunsaturated and 1-alkyl, 2-unsaturated subspecies. This was shown, for example, by the demonstration that human mesangial cells stimulated with TNF produce DAG from PI and regenerate PI in the absence and the presence of PTX. In the latter system there is no evidence to suggest that PA or DAG are derived from sources other than PI. It should be emphasized that the compounds of the invention affect that subset of PAPH and LPAAT that relates to substrates with unsaturated fatty acids other than arachidonate in the sn-2 position, not the housekeeping forms of these enzymes that serve the PI pathway.

Each membrane phospholipid subclass (e.g., PA, PI, PE, PC and PS) reaches a stable content of characteristic fatty acyl side chains due to cyclic remodeling of the plasma membrane as well as turnover for each subclass. PA is often stable, but present in relatively small quantities. PA in resting cells consists mostly of saturated acyl chains, usually consisting of myristate, stearate and palmitate. In resting cells, PC's acyl side chains consist mostly of acyl palmitate in the sn-1 position and oleate in the sn-2 position. PE and PI are predominantly composed of sn-1 stearate and sn-2 arachidonate.

Due to this characteristic content of acyl groups in the sn-1 and sn-2 positions, the origin of any PA species may be deduced from the chemical nature of its acyl groups in the sn-1 and sn-2 positions. For example, if PA is derived from PC through action of the enzyme PLD, the PA will contain the characteristic acyl side chains of PC substrate passed through the second messenger pathway. Further, the origin of any 1,2 sn-substrate species may be differentiated as to its origin. However, it is important to know whether or not each phospholipid species passes through a PA form previous to hydrolysis to DAG. The lyso-PA that is converted to PA and thence to DAG may be shown. The complexities of this second messenger pathway can be sorted by suitable analyses by fatty acyl side chain chemistry (i.e., by thin layer chromatography, gas-liquid chromatography, or high pressure liquid chromatography) of intermediates in cells at various time points after stimulation of the second messenger pathway.

In certain meseachymal cells, such as neutrophils and rat or human mesangial cells, several signaling pathways may be activated in tandem, simultaneously or both. For example, in neutrophils, F-Met-Leu-Phe stimulates formation of PA through the action of PLD, followed in time by formation of DAG through the action of PAPH. Several minutes later, DAG is generated from PI through the classical phosphoinositide pathway. In many cells, DAG is derived from both PA that is being remodeled through a cycle whereby PA is sn-2 hydrolyzed by PLA-2, followed by sn-2 transacylation by LPAAT, and a PLD-pathway from PA that is generated from either PE or PC or both substrates by PLD.

The present second messenger pathway involves substrates with unsaturated fatty acids in the sn-2 position other than arachidonate and those sub species of PAPH and LPAAT that are not involved in normal cellular housekeeping functions that are part of the classical PI pathway. The PAPH and LPAAT enzymes involved in the present second messenger pathway are exquisitely stereo specific for different acyl side chains and isomeric forms of substrates. Therefore, the inventive compounds are preferably, substantially enantiomerically pure, and preferably are the R enantiomer at the chiral carbon atom bonded to the hydroxyl group.

PTX (in vitro) blocks formation of remodeled PA through the PA/DAG pathway at high PTX concentrations (greater than those that could be achieved in patients without dose-limiting side effects) by blocking formation of PA subspecies at LPAAT. Even in the presence of PTX, cells continue to form PA through the action of PLD, and DAG is also formed through the action of phospholipase C on PC and PI. The latter pathway are not inhibited by the inventive compounds or PTX. In PTX-treated cells, DAG derived from remodeled and PLA-generated PA is diminished (e.g. 1,2-sn-dioleoyl DAG, 1-alkyl, 2-linoleoyl DAG and 1-alkyl, 2-docosahexaneolyl DAG). Therefore, the inventive compounds and PTX inhibit the formation of only a certain species of PA and DAG by selectively inhibiting a specific second messenger pathway that is only activated in cells by noxious stimuli, but is not used to signal normal cellular housekeeping functions.

Therapeutic Uses of the Inventive Compounds

The specific activation inhibition of the second messenger pathway, as described above and activated primarily by various noxious stimuli, suggests that the inventive compounds are useful in treating a wide variety of clinical indications, mediated at the cellular level by a common mechanism of action.

The term "treatment" refers to any treatment of a disease or condition in a mammal, particularly a human, and includes, without limitation:

(i) preventing the disease or condition from occurring in a subject which may be predisposed to the condition but has not yet been diagnosed with the condition and, accordingly, the treatment constitutes prophylactic treatment for the pathologic condition;

(ii) inhibiting the disease or condition, i.e., arresting its development; relieving the disease or condition, i.e., causing regression of the disease or condition; or (iii) relieving the symptoms resulting from the disease or condition, e.g., relieving an inflammatory response without addressing the underlining disease or condition.

In vitro and in vivo data, presented herein, provides predictive data that a wide variety of clinical indications, having similar effects on the specific second messenger pathway, may be treated by the inventive compounds, which specifically inhibit the pathway, activated by noxious stimuli and mediated through, for example, inflammatory cytokines. In fact, the mechanism of action for the inventive compounds explains why these compounds have a multifarious clinical indications.

Activation of the second messenger pathway is a major mediator of response to noxious stimuli and results in cellular signals that lead to, for example, acute and chronic inflammation, immune response and cancer cell growth. Although the inventive compounds may desirably inhibit many other unmentioned, noxious stimuli, they most effectively mediate the above conditions. Signals mediated by the present second messenger pathway include, for example, those cellular responses of LPS directly, T cell activation by antigen, B cell activation by antigen, cellular responses to IL-1 mediated through the IL-1 Type 1receptor (but not the IL-1 Type 2 receptor), the TNF Type 1 receptor, growth stimulated by transformations including, but not limited to, activated oncogenes (e.g., ras, abl, her 2-neu and the like), smooth muscle cell proliferation stimulated by PDGF, b-FGF and IL-1; T cell and B cell growth stimulation by IL-2, IL-4 or IL-7 and IL-4 or IL-6, respectively; and more generally, T cell receptor signaling.

In vitro, the inventive compounds: (1) block IL-1 signal transduction through the Type 1 receptor as shown, for example, by preventing IL-1 and IL-1 plus PDGF (platelet derived growth factor) induction of proliferation of smooth muscle, endothelial and kidney mesengial cells; (2) suppress up-regulation of adhesion molecules as shown, for example, by blocking VCAM in endothelial cells; (3) inhibit TNF, LPS and IL-1 induced metalloproteases (an inflammation model); (4) block LPS, TNF or IL-1 induced metalloprotease and secondary cytokine production (for prevention and treatment of septic shock); (5) suppress T cell and B cell activation by antigen, for example, IL-2 and IL-4; (6) inhibit mast cell activation by IgE; (7) are cytotoxic for transformed cells and tumor cell lines, yet not for normal cells; (8) block signaling by IL-2, IL-4, IL-6 and IL-7 on T and B cells; and (9) inhibit IL-12 mediated cell signalling in Th1 cell-mediated disease conditions.

The foregoing in vitro effects give rise to the following in vivo biologic effects, including, but not limited to, protection and treatment of endotoxic shock and sepsis induced by gram positive or gram negative bacteria, inhibition of tumor cell growth, synergistic immunosuppression, active in autoimmune diseases and in suppressing allograft reactions, and stimulation of hair grow through reversal of an apoptotic process. The inventive compounds are most potent when used to prevent and treat septic shock, treat acute and chronic inflammatory disease, treat or prevent an autoimmune disease and stimulate hair growth (when applied topically).

The inventive compounds also are useful as an adjuvant to inhibit toxic side effects of drugs whose side effects are mediated through the present second messenger pathway.

Metalloproteases mediate tissue damage such as glomerular diseases of the kidney, joint destruction in arthritis, and lung destruction in emphysema, and play a role in tumor metastases. Three examples of metalloproteases include a 92 kD type V gelatinase induced by TNF, IL-1 and PDGF plus bFGF, a 72 kD type IV collagenase that is usually constitutive and induced by TNF or IL-1, and a stromelysin/PUMP-1 induced by TNF and IL-1. The inventive compounds can inhibit TNF or IL-1 induction of the 92 kD type V gelatinase inducable metalloprotease. Moreover, the inventive compounds can reduce PUMP-1 activity induced by 100 U/ml of IL-1. Accordingly, the inventive compounds prevent induction of certain metalloproteases induced by IL-1 or TNF and are not involved with constitutively produced proteases (e.g., 72 kD type IV collagenase) involved in normal tissue remodeling.

The inventive compounds inhibit signal transduction mediated through the Type I IL-1 receptor, and are therefore considered as IL-1 antagonists. A recent review article entitled "The Role of Interleukin-1 in Disease" (Dinarello and Wolff *N. Engl. J. Med.* 328, 106, Jan. 14, 1993) described the role of IL-1 as "an important rapid and direct determinant of disease." "In septic shock, for example, IL-1 acts directly on the blood vessels to induce vasodilatation through the rapid production of platelet activating factor and nitric oxide, whereas in autoimmune disease it acts by stimulating other cells to produce cytokines or enzymes that then act on the target tissue." The article describes a group of diseases that are mediated by IL-1, including sepsis syndrome, rheumatoid arthritis, inflammatory bowel disease, acute and myelogenous leukemia, insulin-dependent diabetes mellitus, atherosclerosis and other diseases including transplant rejection, graft versus host disease (GVHD), psoriasis, asthma, osteoporosis, periodontal disease, autoimmune thyroiditis, alcoholic hepatitis, premature labor secondary to uterine infection and even sleep disorders. Since the inventive compounds inhibit cellular signaling through the IL-1 Type I receptor and are IL-1 antagonists, the inventive compounds are useful for treating all of the above-mentioned diseases.

For example, for sepsis syndrome, the mechanism of IL-1-induced shock appears to be the ability of IL-1 to increase the plasma concentrations of small mediator molecules such as platelet activating factor, prostaglandin and nitric oxide. These substances are potent vasodilators and induce shock in laboratory animals. Blocking the action of IL-1 prevents the synthesis and release of these mediators. In animals, a single intravenous injection of IL-1 decreases mean arterial pressure, lowers systemic vascular resistance, and induces leukopenia and thrombocytopenia. In humans, the intravenous administration of IL-1 also rapidly decreases blood pressure, and doses of 300 ng or more per kilogram of body weight may cause severe hypotension. The therapeutic advantage of blocking the action of IL-1 resides in preventing its deleterious biologic effects without interfering with the production of molecules that have a role in homeostasis. The present inventive compounds address the need, identified by Dinarello and Wolff, by inhibiting cellular signaling only through the IL-1 Type I receptor and not through the IL-1 Type II receptor.

With regard to rheumatoid arthritis, Dinarello and Wolff state: "Interleukin-1 is present in synovial lining and synovial fluid of patients with rheumatoid arthritis, and explants of synovial tissue from such patients produce IL-1 in vitro. Intraarticular injections of interleukin-1 induce leukocyte infiltration, cartilage breakdown, and periarticular bone remodeling in animals. In isolated cartilage and bone cells in vitro, interleukin-1 triggers the expression of genes for collagenases as well as phospholipases and cyclooxygenase, and blocking its action reduces bacterial-cell-wall-induced arthritis in rats." Therefore, the inventive compounds, as IL-1 antagonists, are useful to treat and prevent rheumatoid arthritis.

With regard to inflammatory bowel disease, ulcerative colitis and Crohn's disease are characterized by infiltrative lesions of the bowel that contain activated neutrophils and macrophages. IL-1 can stimulate production of inflammatory eicosanoids such as prostaglandin $E_2$ ($PGE_2$) and leukotriene $B_4$ ($LTB_4$) and IL-8, an inflammatory cytokine with neutrophil-chemoattractant and neutrophil-stimulating properties. Tissue concentrations of PGE2 and LTB4 correlate with the severity of disease in patients with ulcerative colitis, and tissue concentrations of IL-1 and IL-8 are high in patients with inflammatory bowel disease. Therefore, an IL-1 antagonist, such as the inventive compounds, would be effective to treat inflammatory bowel disease.

With regard to acute and chronic myelogenous leukemia, there is increasing evidence that IL-1 acts as a growth factor for such tumor cells. Therefore, the inventive compounds should be effective to prevent the growth of worsening of disease for acute and chronic myelogenous leukemias.

Insulin-dependent diabetes mellitus (IDDM) is considered to be an autoimmune disease with destruction of beta cells in the islets of Langerhans mediated by immunocompetent cells. Islets of animals with spontaneously occurring IDDM (e.g. BB rats or NOD mice) have inflammatory cells that contain IL-1. Therefore, the inventive compounds should be useful for the prevention of and treatment of IDDM.

IL-1 also plays a role in the development of atherosclerosis. Endothelial cells are a target of IL-1. IL-1 stimulates proliferation of vascular smooth muscle cells. Foam cells isolated from fatty arterial plaques from hypercholesterolemic rabbits contain IL-1 and IL-1 messenger RNA. The uptake of peripheral blood monocytes results in initiation of IL-1 production by these cells. IL-1 also stimulates production of PDGF. Taken together, IL-1 plays a part in the development of atherosclerotic lesions. Therefore, an IL-1 antagonist, such as the inventive compounds should be useful in preventing and treating atherosclerosis.

IL-1 activates (through the Type I IL-1 receptor) a lyso-PA acyltransferase (LPAAT) and phosphatidate phosphohydrolase within 5 seconds of cell (for example, human mesangial cells, HMC) exposure to this cytokine. Activation of both enzymes results in production of PA species with sn-1 and sn-2 unsaturated acyl groups, with the majority of sn-2 acyl chains being polyunsaturated. Both IL-1 and a product of LPAAT, 1,2-sn-dilinoleoyl PA, activate a signaling pathway involving hydrolysis of PE to PA. This reaction is followed by dephosphorylation of PA to produce both 1,2-sn-diacylglycerol, and 1-o-alkyl or 1-o-alkenyl acylglycerol (AAG) species. The inventive compounds exert their activity by inhibiting one or both enzymes at the inner leaflet of the plasma membrane. Therefore, appropriate in vitro models for drug activity is to measure inhibition of stimulation caused by a pro-inflammatory cytokine or other inflammatory cellular signal.

The generation of the sn-2 unsaturated PA fraction by LPAAT serves to activate either G-proteins, or acts directly upon PLD through alteration of its lipid microenvironment. Activation of LPAAT and generation of the sn-2-unsaturated PA species is an energy sensitive pathway of PLD. This provides a mechanism for a limited-receptor system to amplify a signal and generate a cellular response by rapid synthesis of small amounts of PA. Uptake of di-unsaturated PA, which is about <0.1% of total membrane lipid mass, is sufficient to activate PLD activity. This quantity of PA is similar to that endogeneously synthesized by LPAAT. The PA-stimulated PLD acts upon PE, which should be localized to the inner leaflet of the cell membrane, which is enriched in PE relative to the outer leaflet. Therefore, the cellular inflammatory response to IL-1 is mediated by the pathway: IL-1R→PA→(PLD)→PE. Whereas a localized tissue response is: lysoPA→PI→PKC→(PLD)→PC. The PLD species are likely to be different isozymes. The second messenger pathway whose activation is inhibited by the inventive compounds is not a PI-derived pathway and does not involve PKC in the time courses of inhibition. PKC is acutely activated by PI-derived DAG, but chronic activation (i.e., >30 min) is maintained by PC-derived PA generated by PC-directed PLD. Therefore, the pathway inhibited by the inventive compounds is PE-directed and not PC-directed. Moreover, the PE-directed PLD favors substrates with sn-2 long-chain unsaturation.

DAG and PA are upregulated in oncogenically transformed cells. For example, activating ras mutations result in increased generation of DAG on stimulation with mitogens, although the sources of DAG have differed between experimental systems. In nontransformed renal mesangial cells, IL-1 stimulation increased PLA2 and LPAAT activation, resulting in generation of sn-2 unsaturated PA and subsequent hydrolysis to DAG by phosphatidate phosphohydrolase. The ras transformation in NIH/3T3 cells upregulates serum-stimulated generation of DAG and PA. The specific species of DAG that is stimulated by serum is dioleoyl and for PA are dilinoleoyl and dioleoyl. This upregulation occurs over 4–12 hours and pretreatment of cells with an inventive compound, or PTX, blocks generation of these phospholipid second messengers. The inhibition occurs either through suppressing the generation of PA de novo from lysoPA, or through inhibition of one or both arms of the Lands cycle. The coordinate increase of lysoPA in the setting of diminished PA/DAG production suggests inhibition of transacylation of a precursor lipid. Therefore, the ras transformation mediates an upregulation of PA through indirect stimulation of PLA2 and/or LPAAT activity. The inventive compounds inhibit the conversion of the upregulated lysoPA to PA and subsequently block the phenotypic changes induced by PA/DAG in the membrane.

The ability of the inventive compounds to inhibit generation of unsaturated phospholipids is mirrored by the ability of inventive compounds to inhibit proliferation and tumorogenicity of ras-transformed cells in vitro and in vivo. PTX inhibits ras-transformed NIH/3T3 cells more than parental cells. This inhibition is reversible and is not associated with significant cytotoxicity.

Excessive or unregulated TNF (tumor necrosis factor) production is implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever, myalgias due to infection such as influenza, cachexia secondary to infection, AIDS or malignancy, AIDS, other viral infections (e.g., CMV, influenza, adenovirus, herpes family), keloid formation, scar tissue formation, Crohn's disease, ulcerative colitis, or pyresis. The inventive compounds or pharmaceutically acceptable salts thereof can be used in the manufacture of a medicament for the prophylactic or therapeutic treatment of any disease state in a human or other mammal, which is exacerbated or signaled through the present second messenger cellular phospholipid-based signaling pathway and by excessive or unregulated production of "first messenger" inflammatory cytokines such as TNF or IL-1. With regard to TNF first messenger signaling, there are several disease states in which excessive or unregulated TNF production by monocytes/macrophages is implicated in exacerbating or causing the disease. These include, for example, neurodegenerative diseases such as Alzheimers disease, endotoxemia or toxic shock syndrome (Tracey et al., *Nature* 330:662, 1987 and Hinshaw et al., *Circ. Shock* 30:279, 1990); cachexia (Dezube et al., *Lancet* 355:662, 1990), and adult respiratory distress syndrome (Miller et al., *Lancet* 2(8665):712, 1989). The inventive compounds may be used topically in the treatment of prophylaxis of topical disease states mediated or exacerbated by excessive TNF or IL-1, such as viral infections (herpes or viral conjunctivitis), psoriasis, fungal or yeast infections (ringworm, athletes foot, vaginitis, dandruff, etc.) or other dermatologic hyperproliferative disorders. High TNF levels have been implicated in acute malaria attacks (Grau et al., *N. Engl. J. Med.* 320:1585, 1989), chronic pulmonary inflammatory diseases such as silicosis and asbestosis (Piguet et al., *Nature* 344:245, 1990, and Bissonnette et al., *Inflammation* 13:329, 1989), and reperfusion injury (Vedder et al., *Proc. Natl. Acad. Sci. USA* 87:2643, 1990).

The compounds of the invention can inhibit certain VEGF (vascular endothelial growth factor), FGF (fibroblast growth factor) and PDGF (platelet derived growth factor) effects in vivo, such as inhibition of angiogenesis or restenosis. For example, Ferns et al. (*Science* 253:1129, 1991) have shown that neointimal smooth muscle chemotaxis and angioplasty are inhibited in rats using a neutralizing antibody to PDGF. Also, Jawien et al. (*J. Clin Invest.* 89:507, 1992) have shown that PDGF promotes smooth muscle migration and intimal thickening in a rat model of balloon angioplasty. Inhibition of the PDGF-mediated effects following balloon angioplasty by the inventive compounds is the pharmacological rationale for using the inventive compounds as therapeutic agents to prevent restenosis. The inventive compounds also inhibit atherogenesis because increased levels of PDGF expressed by macrophages are associated with all phases of atherogenesis (Ross et al., *Science* 248:1009, 1990). Further, many human tumors express elevated levels of either PDGF, FGF, receptors for FGF or PDGF, or mutated cellular oncogenes highly homologous to these growth factors or their receptors. For example, such tumor cell lines include sarcoma cell lines (Leveen et al., *Int. J. Cancer* 46:1066, 1990), metastatic melanoma cells (Yamanishi et al., *Cancer Res.* 52:5024, 1992), and glial tumors (Fleming et al., *Cancer Res.* 52:4550, 1992).

Thus, the drugs of the invention are also useful to raise the seizure threshold, to stabilize synapses against neurotoxins such as strychnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

The compounds of the invention further are able to decrease enhanced levels of a relevant PA and DAG resulting from stimulation of synaptosomes with acetylcholine and/or epinephrine. This suggests that the effects of the compounds of the invention are to both enhance the release of inhibitory neural transmitters such as dopamine, and to modulate the distal "slow current" effects of such neurotransmitters.

The inventive compounds are useful in limiting inflammatory responses while leaving the specificity of the immune system, deemed necessary for host protection, intact. These compounds act on IL-12 responsive cells to inhibit cellular processes and activities mediated by IL-12 signalling. The terms "cellular process or activity mediated by IL-12" and "IL-12 mediated processes and activities," as used herein includes IL-12 initiated cellular processes and activities, for example, the direct stimulation of IFN-γ production by resting T cells and NK cells. This term also includes the IL-12 modulation of ongoing processes and activities, for example, the enhancement of anti-CD3 induced IFN-γ secretion. Various other IL-12-mediated processes and activities are intended to be encompassed by this term, for example, the differentiation of naïve T cells into Th1 cells; maintenance of the Th1 phenotype (e.g., high IFN-γ production, low IL-4 production); proliferation of T cell blasts; enhancement of NK cell and CTL cytolytic activity, and the like. For additional examples, see Trinchieri, *Annu. Rev. Immunol.* 13: 251–76 (1995).

IL-12, also referred to as natural killer cell stimulatory factor ("NKSF") or cytotoxic lymphocyte maturation factor ("CLMF"), is a potent immunoregulatory molecule that plays a role in a wide range of diseases. In particular, IL-12 is a heterodimeric cytokine that is produced by phagocytic cells, e.g., monocytes/macrophages, B-cells and other antigen-presenting cells ("APC") and is believed to act as a proinflammatory cytokine. IL-12 is believed to play a specific role in diseases exhibiting an inflammatory component, namely, diseases that exhibit cell-mediated inflammatory responses, such as, multiple sclerosis, diabetes, chronic inflammatory bowel disease, etc.

IL-12 affects both natural killer cells ("NK cells") and T lymphocytes ("T cells"), and stimulates IFN-γ production by both of these cell types. For example, in NK cells, IL-12 stimulates: NK cell proliferation, membrane surface antigen up-regulation, LAK cell generation and NK cell activity elevation; induces IFN-γ and TNF-α production and the growth and expansion of either resting or activated NK cells; and increases soluble p55 and soluble p75 TNF receptor production and NK cell cytotoxicity. See *R&D Systems Catalog*, pp. 67–69 (1995). T cells recognize antigens via interaction of a heterodimeric (alpha/beta, or gamma/delta) receptor with short peptide antigenic determinants that are associated with major histocompatibility complex ("MHC") molecules. T cells can be divided broadly into two functional categories by the presence of two mutually exclusive antigens on their cell surface, CD4 (helper) and CD8 (cytotoxic). The CD4 and CD8 antigens regulate T cell interaction with MHC and their mutually exclusive expression derives from their strict specificity for MHC. Class II MHC-restricted T cells are primarily CD4+ and class I MHC-restricted T cells are CD8+. The T cells further differentiate into helper, cytotoxic and suppressor cells.

As mentioned above, IL-12 also affects T cells, including stimulation of T cell IFN-γ production in response to antigen. While CD8+ T cells are associated with cytotoxicity functions, CD4+ T cells are associated with helper function and secrete various cytokines that regulate and modulate immune responses. CD4+ T cells can be further subdivided into T helper 1 (Th1) and T helper 2 (Th2) subsets, according to the profile of cytokines they secrete. Therefore, Th1 cells produce predominantly inflammatory cytokines, including IL-2, TNF-α and IFN-γ, while Th2 cells produce anti-inflammatory cytokines such as IL-4, IL-5, IL-10 and IL-13 that are linked to B cell growth and differentiation.

The Th1 and Th2 CD4+ T cell subsets are derived from a common progenitor cell, termed Th0 cells. During an initial encounter with an antigen, the differentiation into Th1 and Th2 is controlled by the opposing actions of two key cytokines, namely IL-12 and IL-4, which induce the differentiation of Th0 into Th1 and Th2, respectively. The development of Th1 and Th2 cells is primarily influenced by the cytokine milieu during the initial phase of the immune response, in which IL-12 and IL-4, respectively, play decisive roles. The cytokines produced by each Th-cell phenotype are inhibitory for the opposing phenotype. For example, Th1 cytokines enhance cell-mediated immunities and inhibit humoral immunity. Th2 cytokines enhance humoral immunity and inhibit cell-mediated immunities. Trembleau et. al., See *Immunology Today* 16(8): 383–386 (1995).

Furthermore, CD4+ Th1 cells play a role in the pathogenesis of immunological disorders. These cells primarily secrete cytokines associated with inflammation such as IFN-γ, TNF-α, TNF-β and IL-2. IFN-γ is an important component of the inflammatory response and resultant pathology of those diseases exhibiting an inflammatory response. Heremans, et al. In addition to its role in inflammatory response, IFN-γ also contributes to phagocytic cell activation (i.e., macrophage activation), and up-regulation of MHC expression on the surface of antigen-presenting cells ("APC") and other cells. Further, this cytokine is implicated generally in inflammatory immune responses, and in autoimmune diseases, such as multiple sclerosis ("MS"), specifically. See Owens et al., *Neurologic Clinics*, 13(1):51–73 (1995). Furthermore, steroid treatment broadly attenuates cytokine production, but it cannot modulate it selectively, e.g., just the Th0, the Th1 or the Th2 pathways.

IL-12 plays a role in the induction of Th1-cell-mediated autoimmunity. Recent evidence points to a critical role for IL-12 in the pathogenesis of rodent models of Th1 mediated autoimmune diseases such as type-1 diabetes, multiple sclerosis, rheumatoid arthritis, inflammatory bowel disease, and acute graft-versus-host disease. Thus, Th1 cells are believed to be involved in the induction of experimental autoimmune diseases, as demonstrated in adoptive transfer experiments demonstrating the CD4+ cells producing Th1 type lymphokines can transfer disease, as shown in models of experimental autoimmune disease, such as experimental allergic encephalomyelitis ("EAE") (also known as experimental allergic encephalitis) and insulin-dependent diabetes mellitus ("IDDM"). See Trinchieri, *Annu. Rev. Immunol.* 13(1):251–276 (1995). For instance, EAE is an inflammatory T cell mediated, paralytic, demyelinating, autoimmune disease that can be induced in a number of rodents as well as primates. Owens et al. supra. One of the ways that EAE can be induced is by immunization of animals with myelin basic protein ("MBP"). Likewise, administration of IL-12 induces rapid onset of IDDM in 100% of NOD female mice. Trinchieri, supra.

In Vitro Assays for Physiologic and Pharmacological Effects of the Inventive Compounds Various in vitro assays can be used to measure effects of the inventive compounds to module immune activity and have antitumor activity using a variety of cellular types. For example, a mixed lymphocyte reaction (MLR) provides a valuable screening tool to determine biological activity of each inventive compound. In the MLR, PBMCs (peripheral blood mononuclear cells) are obtained by drawing whole blood from healthy volunteers in a heparinized container and diluted with an equal volume of hanks balanced salt solution (HBSS). This mixture is layered on a sucrose density gradient, such as a Ficoll-Hypaque® gradient (specific gravity 1.08), and centrifuged at 1000×g for 25 minutes at room temperature or cooler. PBMC are obtained from a band at a plasma-Ficoll interface, separated and washed at least twice in a saline solution, such as HBSS. Contaminating red cells are lysed, such as by ACK lysis for 10 min at 37° C., and the PBMCs are washed twice in HBSS. The pellet of purified PBMCs is resuspended in complete medium, such as RPMI 1640 plus 20% human inactivated serum. Proliferative response of PBMC to allogeneic stimulation is determined in a two-way MLR performed in a 96-well microtiter plate. Briefly, approximately $10^5$ test purified PBMC cells in 200 1 complete medium are co-cultured with approximately $10^5$ autologous (control culture) or allogeneic (stimulated culture) PBMC cells, wherein the allogeneic cells are from HLA disparate individuals. Varying doses of compounds (drug) are added at the time of addition of cells to the microtiter plate. The cultures are incubated for 6 days at 37° C. in a 5% $CO_2$ atmosphere. At the conclusion of the incubation tritiated thymidine is added (for example, 1 Ci/well of 40 to 60 Ci/mmole) and proliferation determined by liquid scintillation counting.

Another assay for measuring activity of the inventive compounds involves determining PDGF, FGF or VEGF proliferative response using either mouse NIH-3T3 (Balb) cells or human-derived stromal cells. Human stromal cells are plated (e g., about 2000 cells per well) in defined media (e.g., 69% McCoy's, 12.5% fetal calf serum, 12.5% horse serum, 1% antibiotics, 1% glutamine, 1% vitamin supplement, 0.8% essential amino acids, 1% sodium pyruvate, 1% sodium bicarbonate, 0.4% non-essential amino acids and 0.36% hydrocortisone). Two to three days later, the stromal cells are starved in serum-free media. Twenty four hours later, the cells are treated with a stimulating agent, such as PDGF-AA, PDGF-BB or basic FGF (fibroblast growth factor) with or without IL-1 or TNF, and tritiated thymidine. Cell proliferation is determined by liquid scintillation counting.

A B-cell proliferation assay determines the effect of the inventive compounds on inhibiting proliferation of stimulated B-cells, stimulated by an anti-mu antibody (40 g/ml), IL-4 or PMA (2.5 nM). Ramos B-cell tumor cells or murine splenocytes can be incubated with a stimulating agent, an inventive compound and tritiated thymidine to measure inhibition of cell proliferation caused by the stimulating agent.

Assays for the effect of the inventive compounds on IL-12 signalling are described herein in Examples 10 and 11.

Compounds of the Invention

The inventive compounds, and pharmaceutical compositions thereof, for use in the methods of this invention have the formula:

(R)$_j$—(CORE MOIETY), including resolved enantiomers and/or diastereomers, hydrates, salts, solvates and mixtures thereof, wherein j is an integer from one to three, the core moiety comprises a bicyclic ring structure having at least one heterocyclic ring that contains five to six ring atoms and up to two nitrogen heteroatoms, wherein R may be selected from the group consisting of hydrogen, halogen (preferably bromine, chlorine, fluorine and iodine), hydroxyl, amino, substituted or unsubstituted benzyl, alkyl ($C_{1-6}$, preferably methyl) or alkenyl ($C_{1-6}$), preferably the alkyl or alkenyl groups being substituted by an hydroxy, halogen and dimethylamine and/or interrupted by an oxygen atom. Preferred R include, but are not limited to, methyl, ethyl, isopropyl, n-propyl, isobutyl, n-butyl, t-butyl, 2-hydroxyethyl, 3-hydroxypropyl, 3-hydroxy-n-butyl, 2-methoxyethyl, 4-methoxy-n-butyl, 5-hydroxyhexyl, 2-bromopropyl, 3-dimethylaminobutyl, 4-chloropentyl, and the like. Particularly preferred R are ethyl, methyl, or H, and most preferably, methyl or H. At least one R has the formula I:

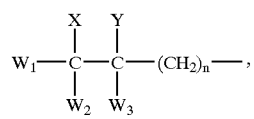

wherein n is an integer from one to twenty, preferably 3 to 20 or 4 to 20, more preferably from 6 to 12, 9 to 15 or 8 to 20, and at least one of X or Y is —OH. If only one of X or Y is —OH, then the other X or Y is hydrogen, $CH_3$—, $CH_3$—$CH_2$—, $CH_3$—$(CH_2)_2$—, or $(CH_3)_2$—$CH_2$—, and $W_1$, $W_2$, and $W_3$ are independently hydrogen, $CH_3$—, $CH_3$—$CH_2$—, $CH_3$—$(CH_2)_2$—, or $(CH_3)_2$—$CH_2$—, wherein X, Y, $W_1$, $W_2$, and $W_3$ alkyl groups may be substituted by an hydroxyl, halo or dimethylamino group and/or interrupted by an oxygen atom, hydrogen or alkyl ($C_{1-4}$). Preferably, n is an integer from seven to twelve. Especially preferred compounds have X and Y both being —OH and each of $W_1$, $W_2$, and $W_3$ being hydrogen or methyl. Preferably R having formula I structure is bonded to a ring nitrogen.

Exemplary bicyclic core moieties include, without limitation, substituted or unsubstituted: xanthinyl, dioxotetrahydropteridine, phthalimide, homophthalimide, benzoyleneurea and quinazoline-4(3H)-one. In one preferred embodiment, the core moiety is xanthine or a xanthine derivative.

Especially preferred xanthine compounds have the following formula II:

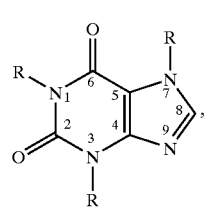

wherein R is selected from the foregoing members. Most preferably, a single R having formula I above is bonded to the $N_1$ xanthine nitrogen in formula II or each of two formula I R are bonded to $N_1$ and $N_7$ xanthine nitrogens, respectively. Remaining R substituents are preferably selected from the group consisting of hydrogen, methyl, fluoro, chloro and amino wherein R is selected from the foregoing members. Preferably, a single R having formula I above is bonded to the $N_1$ xanthine nitrogen in formula II or each of two formula I R are bonded to $N_1$ and $N_7$ xanthine nitrogens, respectively. Remaining R substituents are preferably selected from the group consisting of hydrogen, methyl, fluoro, chloro and amino.

Exemplary methods and examples for preparing the inventive compounds for use in this invention are described in U.S. application Ser. No. 08/756,703, and are incorporated by reference herein in their entirety.

The compounds of the invention may be provided as enantiomeric or diastereomeric mixtures or in resolved or partially resolved forms. Standard procedures are used for resolving optical isomers. Different enantiomeric variants (e.g., stereoisomers and chiral forms) of the inventive compound may have different drug activities, based upon their differential ability to inhibit PAPH and LPAAT. An optical isomer, substantially free of the corresponding enantiomer and/or diastereomers, is at least about 85% of a relevant optical isomer, preferably at least about 95% relevant optical isomer and especially at least about 99% higher relevant optical isomer. Most preferably an amount of other optical forms is undetectable.

To a certain extent, chain length may be useful in predicting degree of activity of the compounds. For example, when n is 2 or less, the compounds show little activity in exemplary assays used herein. When n is 3 or 4, more activity is observed, particularly inhibitive activity in proliferation assays described herein. When n is 6 there is moderate activity. Activity increases significantly (on a potency basis) when n is 7 or greater. A steep-rising curve is apparent for compounds having n equal to 7, 8 or more.

Exemplary, preferred compounds of the invention include both R and S enantiomers and racemic mixtures of the following compounds:

| | | |
|---|---|---|
| 1104 | N-(5,6-Dihydroxyhexyl) phthalimide | 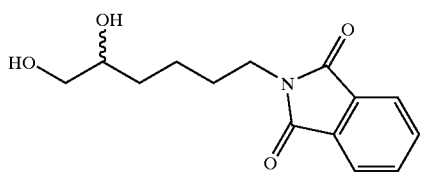 |
| 1106 | N-(8,9-Dihydroxynonyl) phthalimide | 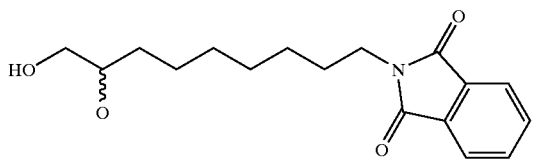 |
| 1108 | N-(10,11-Dihydroxy-undecyl)phthalimide | 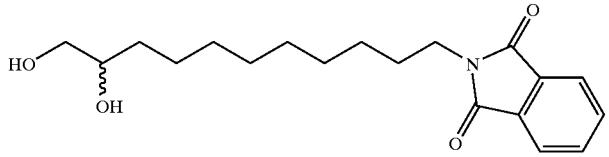 |
| 1113 | N-(10,11-Dihydroxy-undecyl) homophthalimide | 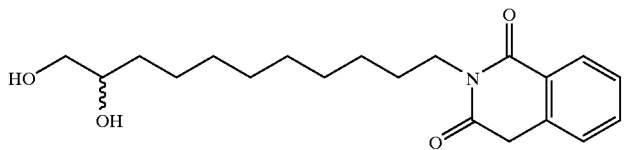 |
| 1118 | N-(9-Phthalimidononyl) phthalimide | 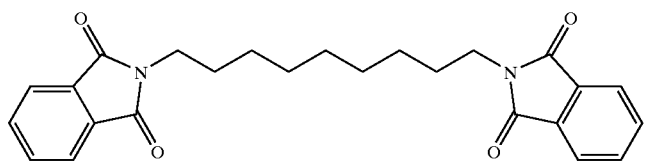 |
| 1204 | 1-(5,6-Dihydroxyhexyl)-3-methylbenzoyleneurea | 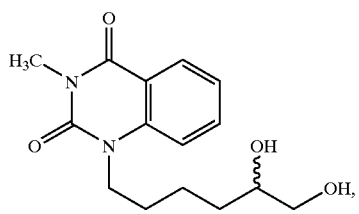 |

-continued
| | | |
|---|---|---|
| 1207 | 1-(5-Hydroxyhexyl)-3-methylbenzoyleneurea | 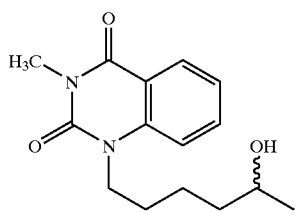 |
| 1215 | 3-(11,10-Dihydroxy-undecyl)quinazoline-4(3H)-one | 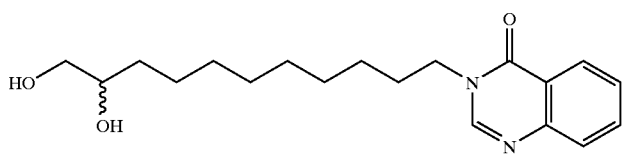 |
| 1401 | 1-(5-Hydroxy-5-methyl-hexyl)-3-methylxanthine | 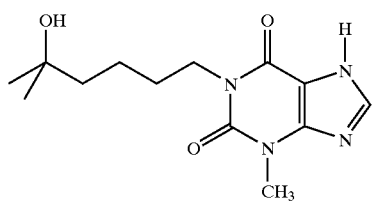 |
| 1402 | 1-(5-Hydroxy-5-methyl-hexyl)-3-methyl-7-ethoxymethylxanthine | 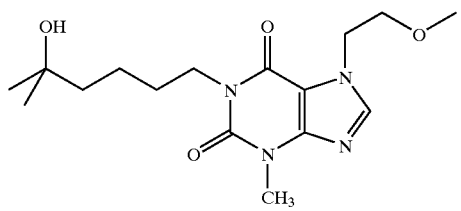 |
| 1407 | 1-(10,11-Dihydroxy-undecyl)-3-methyl-7-methylpivaloylxanthine | 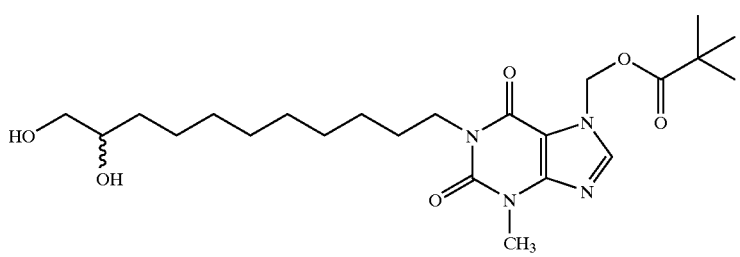 |
| 1408 | 1-(10,11-Dihydroxy-undecyl)-3-methylxanthine | 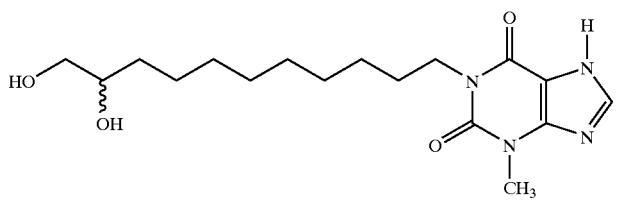 |
| 1417 | 1-(10-Hydroxyundecyl)-3-methylxanthine | 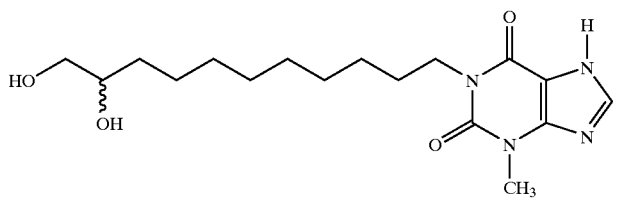 |

-continued
| | | |
|---|---|---|
| 1420 | 7-(10,11-Dihydroxy-undecyl)-1,3-dimethyl-xanthine | 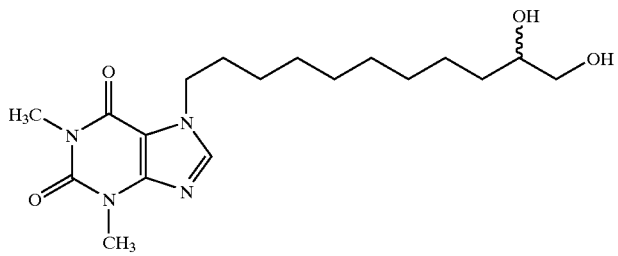 |
| 1428 | 3-(11,10-Dihydroxy-undecyl)-1-methyl-2,4-dioxotetrahydropteridine | 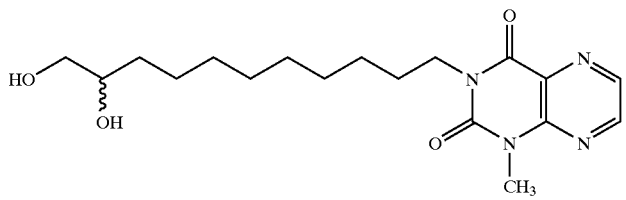 |
| 1429 | 3-(10)-Hydroxyundecyl)-1-methyl-2,4-dioxotetrahydropteridine | 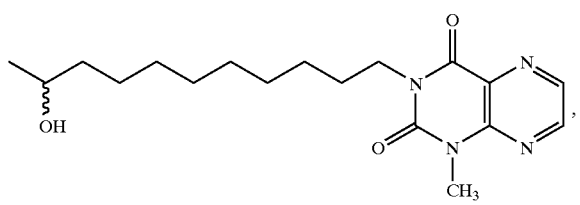 |
| 1440 | 1-(5,6-Dihydroxyhexyl)-3-methylxanthine | 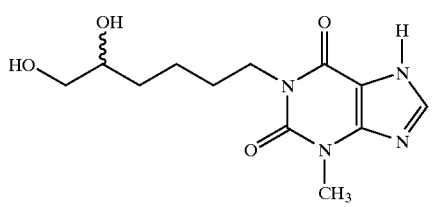 |
| 1444 | 1-(10-Hydroxyundecyl)-3-methyl-7-methylpivaloyl-xanthine | 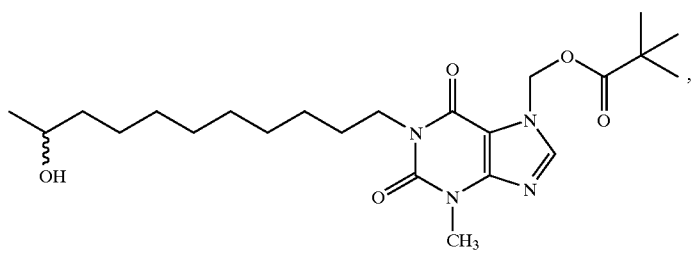 |
| 1528 | 1-(6,7-Dihydroxynonyl)-3,7-dimethylxanthine | 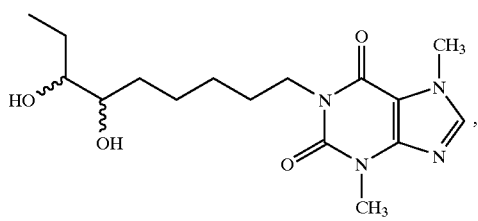 |
| 1536 | 1-(7-Hydroxyoctyl)-3,7-dimethylxanthine | 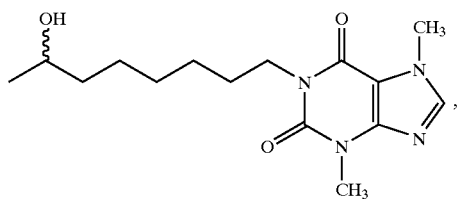 |

-continued
| | | |
|---|---|---|
| 1538 | 1-(7,8-Dihydroxyoctyl)-3,7-dimethylxanthine | 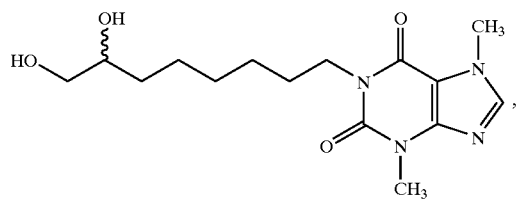 |
| 1540 | 1-(2,3-Dihydroxypropyl)-3,7-dimethylxanthine | 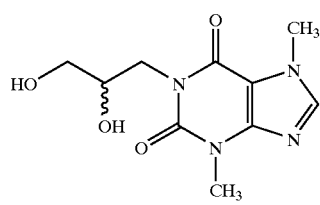 |
| 1542 | 1-(4-Hydroxypentyl)-3,7-dimethylxanthine | 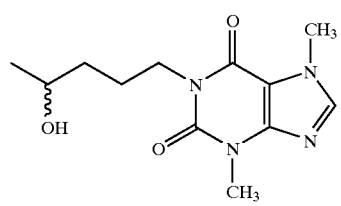 |
| 1544 | 1-(4-Hydroxybutyl)-3,7-dimethylxanthine | 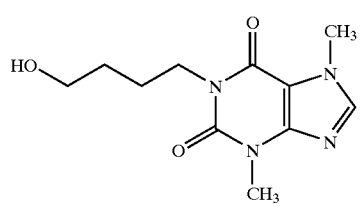 |
| 1545 | 1-(7-Hydroxyheptyl)-3,7-dimethylxanthine | 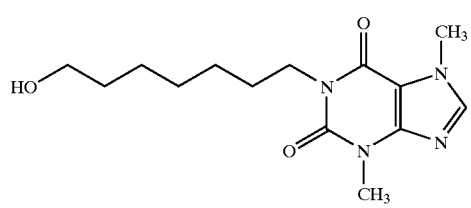 |
| 1546 | 1-(8-Hydroxyoctyl)-3,7-dimethylxanthine | 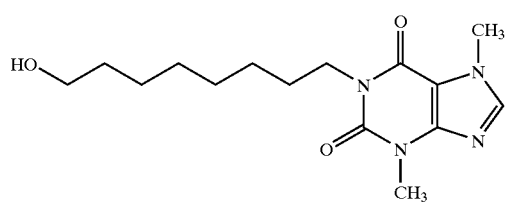 |
| 1551 | 1-(8-Hydroxynonyl)-3,7-dimethylxanthine | 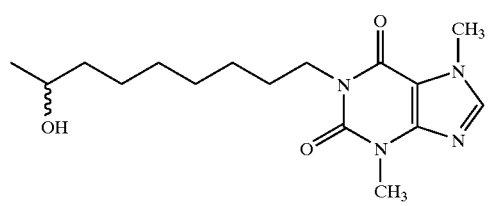 |

-continued
| | | |
|---|---|---|
| 1552 | 1-(9-Hydroxydecyl)-3,7-dimethylxanthine | 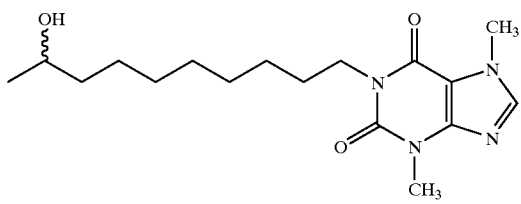 |
| 1556 | 1-(6-Hydroxyhexyl)-3,7-dimethylxanthine | 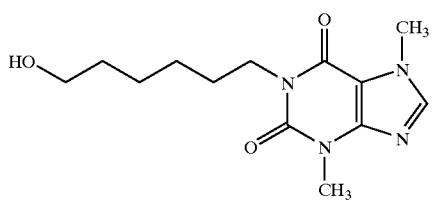 |
| 1559 | 1-(10-Hydroxydecyl)-3,7-dimethylxanthine | 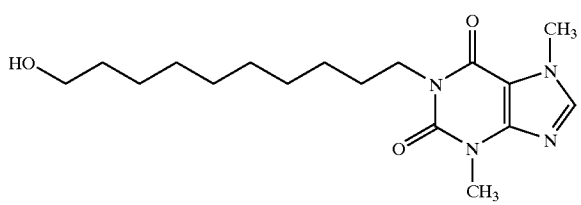 |
| 1561 | 1-(8,9-Dihydroxynonyl)-3,7-dimethylxanthine | 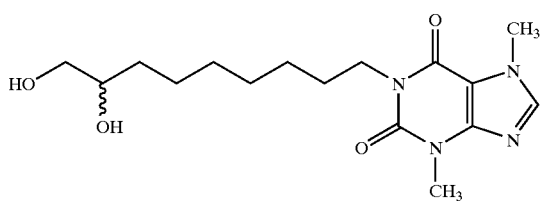 |
| 1564 | 1-(9,10-Dihydroxydecyl)-3,7-dimethylxanthine | 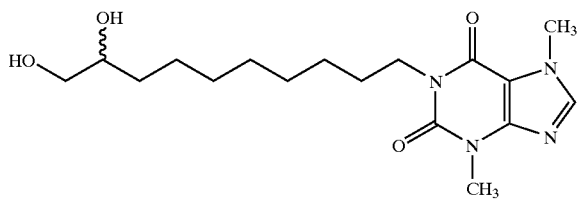 |
| 1566 | 1-(5-Hydroxy-S-methylhexyl)-3,7-dimethylxanthine | 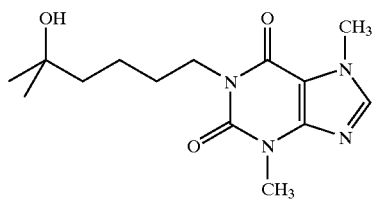 |
| 1584 | 1-(4,5-Dihydroxypentyl)-3,7-dimethylxanthine | 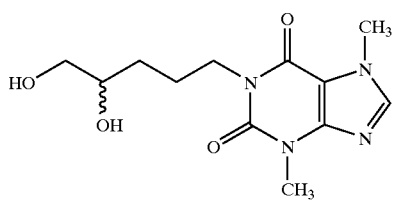 |

-continued
| | | |
|---|---|---|
| 1585 | 1-(6,7-Dihydroxyheptyl)-3,7-dimethylxanthine | 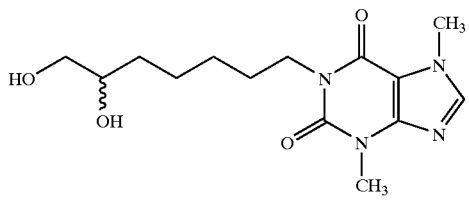 |
| 1587 | 1-(10-Hydroxyundecyl)-3,7-dimethylxanthine | 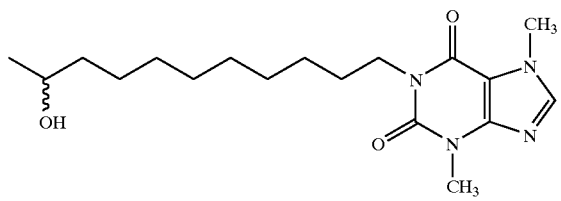 |
| 1592 | 1-(10,11-Dihydroxy-undecyl)-3,7-dimethylxanthine | 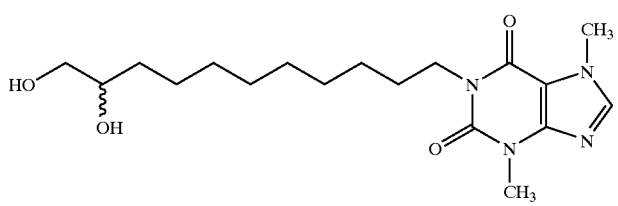 |
| 1597 | 1-(3-(R)-Methyl-7-methyl-6,7-dihydroxyoctyl)-3,7-dimethylxanthine | 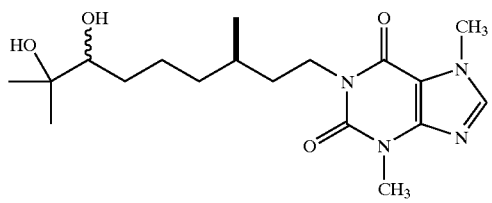 |
| 1597 | 1-(3-(S)-Methyl-7-methyl-6,7-dihydroxyoctyl)-3,7-dimethylxanthine | 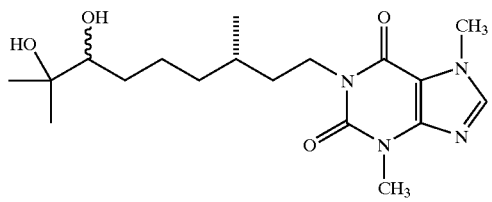 |
| 1598 | 1-(5-Hydroxypentyl)-3,7-dimethylxanthine | 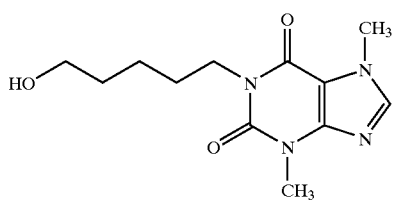 |
| 1599 | 1-(6-Hydroxyheptyl)-3,7-dimethylxanthine | 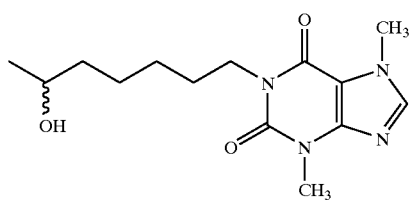 |

-continued
| | | |
|---|---|---|
| 2509 | 1-(3,4-Dihydroxybutyl)-3,7-dimethylxanthine | 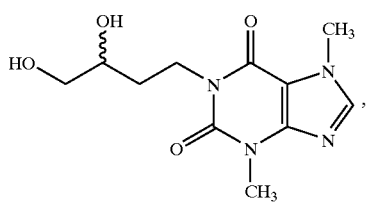 |
| 2520 | 1-(11-Hydroxydodecenyl)-3,7-dimethylxanthine | 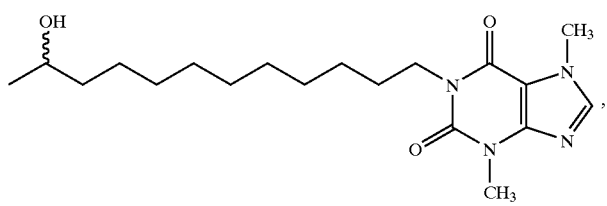 |
| 2517 | 1-(11,12-Dihydroxy-dodecyl)-3,7-dimethylxanthine | 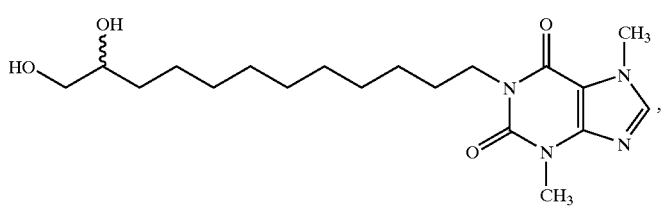 |
| 2537 | 1-(4-(R)-Methyl-7,8-dihydroxy-8-methylnonyl)-3,7-dimethylxanthine | 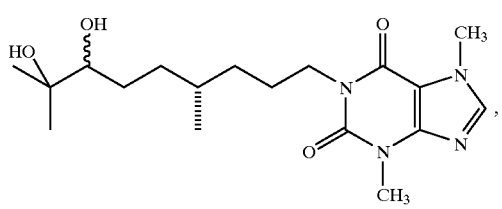 |
| 2537 | 1-(4-(S)-Methyl-7,8-dihydroxy-8-methylnonyl)-3,7-dimethylxanthine | 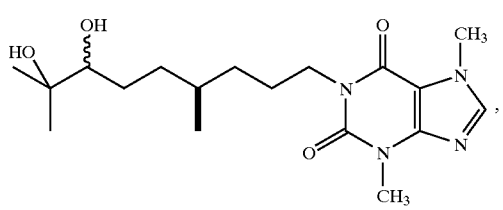 |
| 2540 | 1-(9,10-Dihydroxy-octadecyl)-3,7-dimethylxanthine | 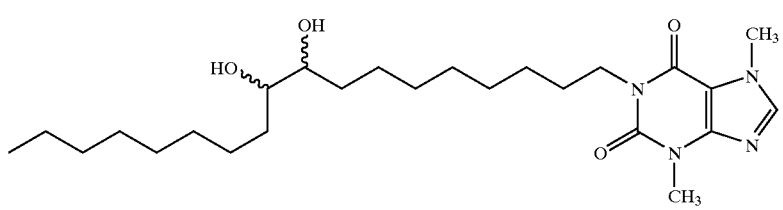 |
| 2546 | 1-(3,7-Dimethyl-2,3,6,7-tetrahydroxyoctyl)-3,7-dimethylxanthine | 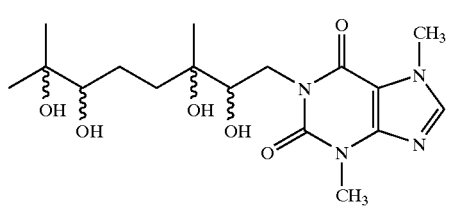 |

-continued
| 2556 | 1-(12,13-Dihydroxy-undecyl)-3,7-dimethylxanthine | 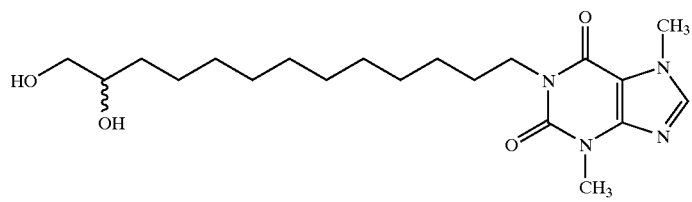 |
| 2568 | 1-(7,8-Dihydroxydecyl)-3,7-dimethylxanthine | 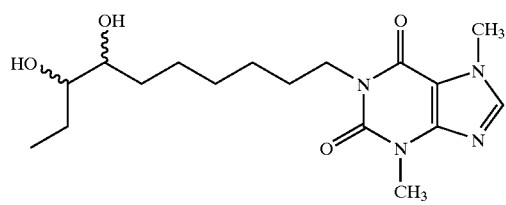 |
| 2569 | 1-(12-Hydroxytridecyl)-3,7-dimethylxanthine | 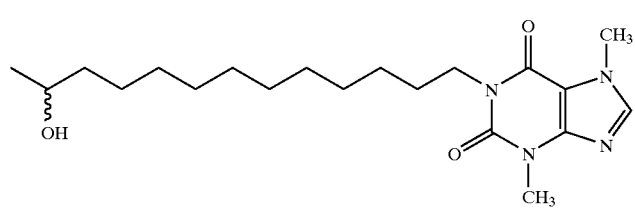 |
| 2595 | 1-(13,14-Dihydroxy tetradecyl)-3,7-dimethylxanthine | 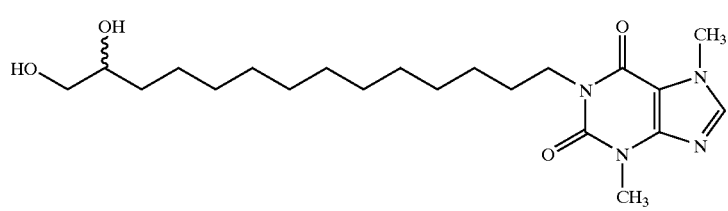 |
| 3504 | 1-(13-Hydroxytetradecyl)-3,7-dimethylxanthine | 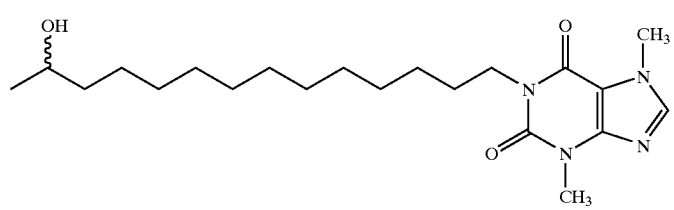 |
| 3514 | 1-(16,17-Dihydroxyheptadecyl)-3,7-dimethyl-xanthine | 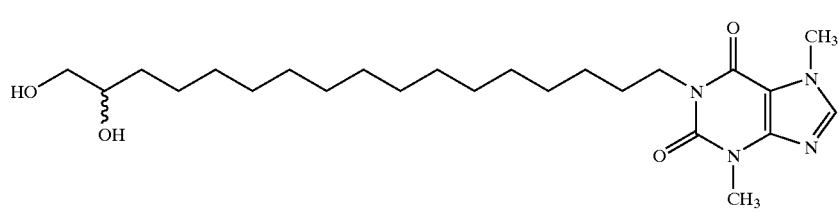 |
| 3515 | 1-(5-Hydroxyheptyl)-3,7-dimethylxanthine | 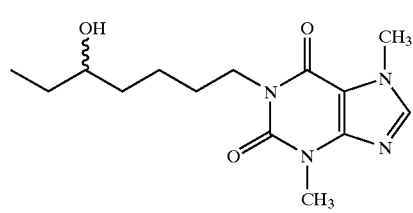 |

-continued

| | | |
|---|---|---|
| 3518 | 1-(16-Hydroxyhepta-decyl)-3,7-dimethyl-xanthine | 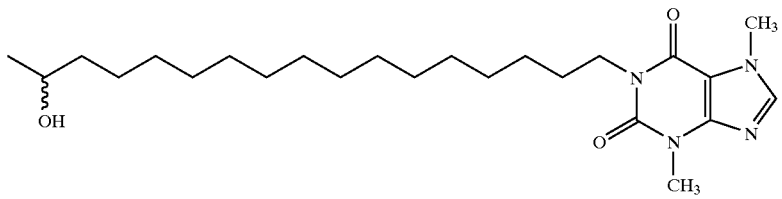 |
| 3520 | 1-(10-Hydroxyeicosyl)-3,7-dimethylxanthine | 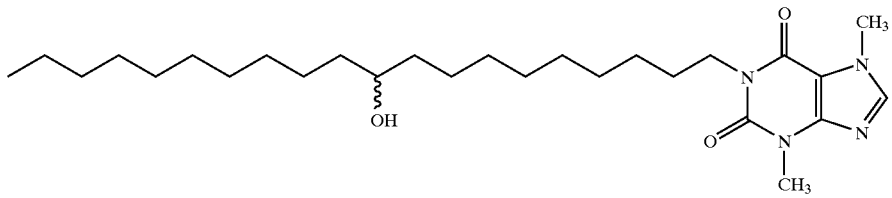 |
| 3524 | 1-(5-Hydroxy-4-methyl-pentyl)-3,7-dimethyl-xanthine | 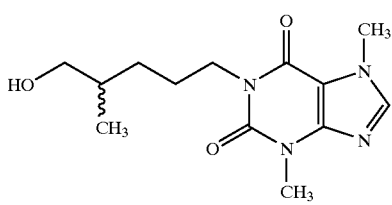 |
| 3539 | 1-(9-Hydroxynonyl)-3,7-dimethylxanthine | 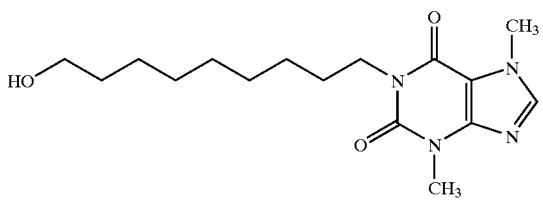 |
| 3540 | 1-(11-Hydroxyundecyl)-3,7-dimethylxanthine | 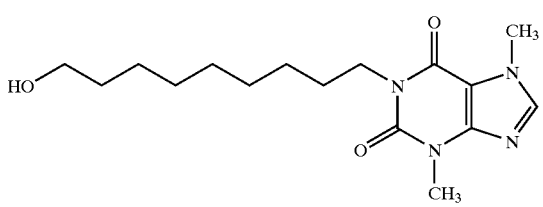 |
| 3553 | 1-(4-Hydroxyhexyl)-3,7-dimethylxanthine | 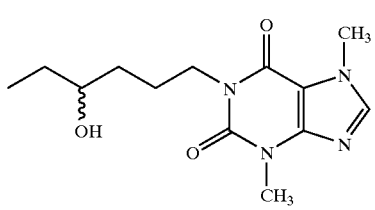 |

For use in the methods of this invention, the compounds are typically administered as a pharmaceutical compositions comprising one or more inventive compounds and a pharmaceutically acceptable carrier or excipient The terms "pharmaceutically effective" or "therapeutically effective" amount of a compound of the present invention is an amount that is sufficient to effect treatment, as defined above, when administered to a mammal in need of such treatment. The amount will vary depending upon the subject and disease condition being treated, the weight and age of the subject, the severity of the disease condition, the manner of administration and the like, which can be readily determined by one of skill in the art. The pharmaceutical composition may be formulated for oral, parenteral or topical administration to a patient.

Treatment of individuals with an inventive compound or pharmaceutical composition may include contacting cells from the individual to be treated with the inventive compound in vitro (e.g., an ex vivo treatment), or administering the inventive compound or pharmaceutical composition via a suitable route to the individual whose cells are to be treated.

Coadministration With a P-450 Inhibitor

The coadministration in vivo of the compounds of the invention along with an inhibitor of P-450 results in an enhanced effect due to a longer half life of the inventive compounds. This in vivo effect is due to the inhibition of a degradation pathway for the compounds of the invention; in particular with respect to dealkylation at the N7 position of the xanthine core. For example, NIH3T3-D5C3 cells can be used to compare effects of a compound of Formula I alone or in combination with a P-450 inhibitor by comparing transformation phenotype among control, incubation with a compound of Formula 1 alone, and coincubation of a compound of Formula 1 with the P-450 enzyme inhibitor.

Compounds that inhibit P-450 include, for example, (mg range daily dosage) propranolol (20–100), metaprolol (20–100); verapamil (100–400), diltiazem (100–400), nifedipine (60–100); cimetidine (400–2,400); ciprofloxacin (500–2000), enoxacin (500–2,000), norfloxacin (500–2000), ofloxacin (500–2,000), pefloxacin (500–2,000); erythromycin (100–1,000), troleandomycin (100–1,000); ketoconizole (100–2,000), thiabenzadole (100–1,000); isoniazid (100–1000); mexiletine (100–1,000); and dexamethasone (1–100 mg).

Pharmaceutical Formulations

A suitable formulation will depend on the nature of the disorder to be treated, the nature of the medicament chosen, and the judgment of the attending physician. In general, the inventive compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

The inventive compounds and their pharmaceutically acceptable salts can be employed in a wide variety of pharmaceutical forms. The preparation of a pharmaceutically acceptable salt will be determined by the chemical nature of the compound itself, and can be prepared by conventional techniques readily available. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram, wherein the amount of inventive compound per dose will vary from about 25 mg to about 1 gram for an adult. When a liquid carrier is used, the preparation will be in the form of a syrup, emulsion, soft gelatin capsule, sterile injectable liquid such as an ampule or nonaqueous liquid suspension. Where the inventive composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions of suspensions may be considered, for example, aqueous gums, celluloses, silicates or oils and are incorporated in a soft gelatin capsule shell. A syrup formulation will generally consist of a suspension or solution of the compound or salt thereof in a liquid carrier (e.g., ethanol, polyethylene glycol, coconut oil, glycerine or water) with a flavor or coloring agent.

The amount of inventive compound required for therapeutic effect on topical administration will, of course, vary with the compound chosen, the nature and severity of the disease and the discretion of the treatment provider. Parenteral includes intravenous, intramuscular, subcutaneous, intranasal, intrarectal, intravaginal or intraperitoneal administration. Appropriate dosage forms for such administration may be prepared by conventional techniques. A typical parenteral composition consists of a solution or suspension of the inventive compound or a salt thereof in a sterile or non-aqueous carrier optionally containing a parenterally acceptable oil, for example polyethylene glycol, polyvinylpyrrolidone, lecithin, arachis oil, or sesame oil. The daily dosage for treatment of sepsis or another severe inflammatory condition via parenteral administration is suitable from about 0.001 mg/kg to about 40 mg/kg, preferably from about 0.01 mg/kg to about 20 mg/kg of an inventive compound or a pharmaceutically acceptable salt thereof calculated as the free base.

The inventive compounds may be administered orally. The daily dosage regimen for oral administration is suitably from about 0.1 mg/kg to about 1000 mg/kg per day. For administration the dosage is suitably form about 0.001 mg/kg to about 40 mg/kg of the inventive compound or a pharmaceutically acceptable salt thereof calculated as the free base. The active ingredient may be administered from 1 to 6 times a day, sufficient to exhibit activity.

The inventive compounds may be administered by inhalation (e.g., intranasal or oral). Appropriate dosage forms include an aerosol or a metered dose inhaler, as prepared by conventional techniques. The daily dosage is suitably form about 0.001 mg/kg to about 40 mg/kg of the inventive compound or a pharmaceutically acceptable salt thereof calculated as the free base. Typical compounds for inhalation are in the form of a solution, suspension or emulsion that may be administered as a dry powder or in the form of an aerosol using a conventional propellant.

EXAMPLES

In order to further illustrate the present invention and advantages thereof, the following specific examples are given but are not meant to limit the scope of the claims in any way. In these examples PTX means Pentoxifylline.

Example 1

This example illustrates the effect of compounds nos. 1551 and 1559 as an immune modulator. FIG. 1 shows a mixed lymphocyte reaction of PTX and two inventive compounds nos. 1551 and 1559 (see above for chemical names and structures). The mixed lymphocyte reaction shows a proliferative response of PBMC (peripheral blood mononuclear cells) to allogeneic stimulation determined in a two-way mixed lymphocyte reaction, described above. Each of the inventive compounds tested was more effective and more potent than PTX in this immune modulating activity assay procedure.

Example 2

Figure 2:
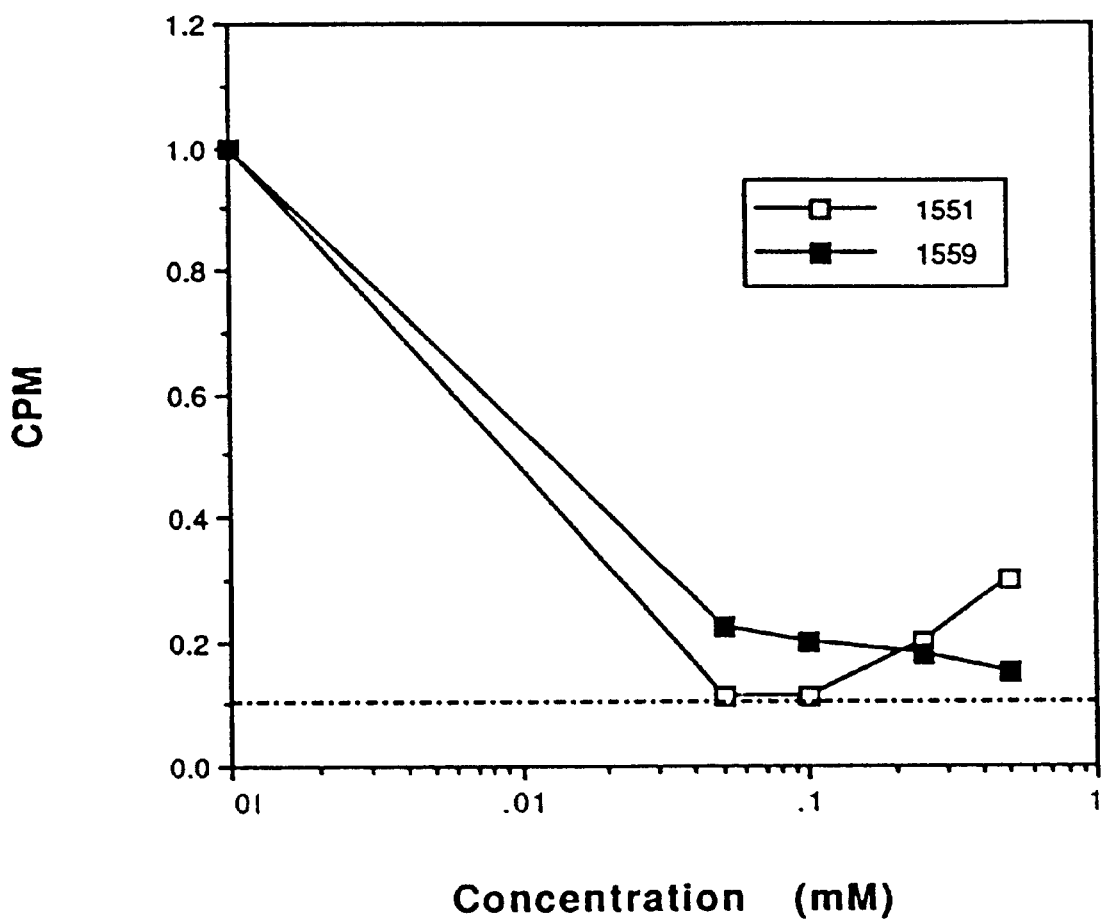
FIG. 2 shows a comparison of inventive compounds nos. 1551 and 1559 on PDGF-induced (platelet derived growth factor) proliferation of human stromal cells. Human stromal cells were starved in serum-free media for 24 hours and then stimulated with 50 ng/ml of PDGF-BB. The drugs were added at various indicated concentrations one hour prior to PDGF stimulation. Both inventive compounds 1551 and 1559 inhibited PDGF-induced stimulation.

This example illustrates a comparison of compounds nos. 1551 and 1559 on PDGF-induced (platelet derived growth factor) proliferation of human stromal cells. Human stromal cells were starved in serum-free media for 24 hours and then stimulated with 50 ng/ml of PDGF-BB. The drugs were added at various indicated concentrations one hour prior to PDGF stimulation. Tritiated thymidine was added at the time of PDGF stimulation. The cells were harvested and counted by liquid scintillation 24 hours after stimulation with PDGF. As shown in FIG. 2, both compound nos. 1551 and 1559 inhibited PDGF-induced stimulation. Background counts (i.e., starved cells) were approximately 10% of control levels.

Example 3

Figure 3:
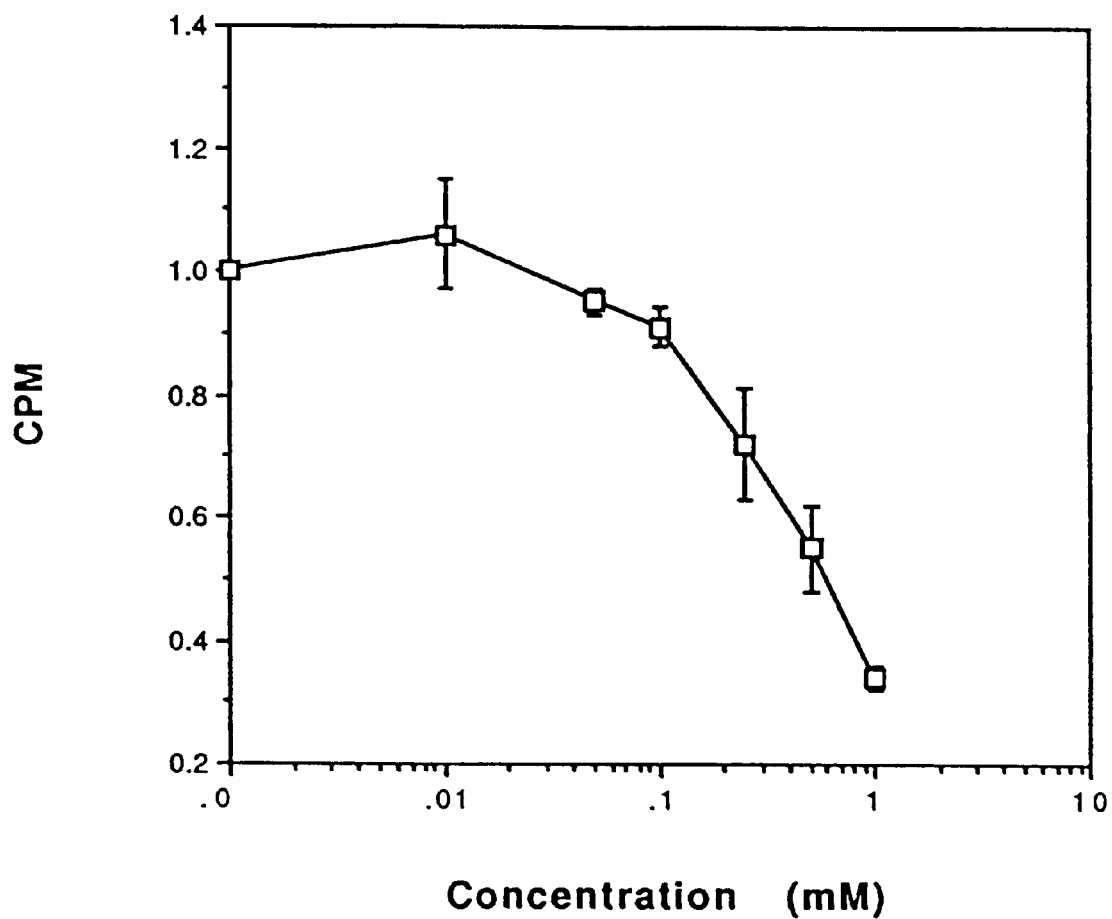
FIG. 3 shows cytotoxicity of inventive compound no. 1559 on LD-2 cells, a human malignant melanoma cell line. The cells were treated with various concentrations of inventive compound no. 1559 and later stained for cell viability with a fluorescent stain. Inventive compound no. 1559 is cytotoxic at higher concentrations, and thus shows anti-tumor activity.

This example provide data from an experiment measuring compound no. 1559 cytotoxicity on LD-2 cells, a human malignant melanoma cell line. The cells were treated with various concentrations of compound no. 1559 and later stained for cell viability with a fluorescence stain (BCECF) and analyzed using a Milipore fluorescence plate reader. As shown in FIG. 3, compound no. 1559 is cytotoxic at higher concentrations, and thus shows antitumor activity.

Example 4

Figure 4:
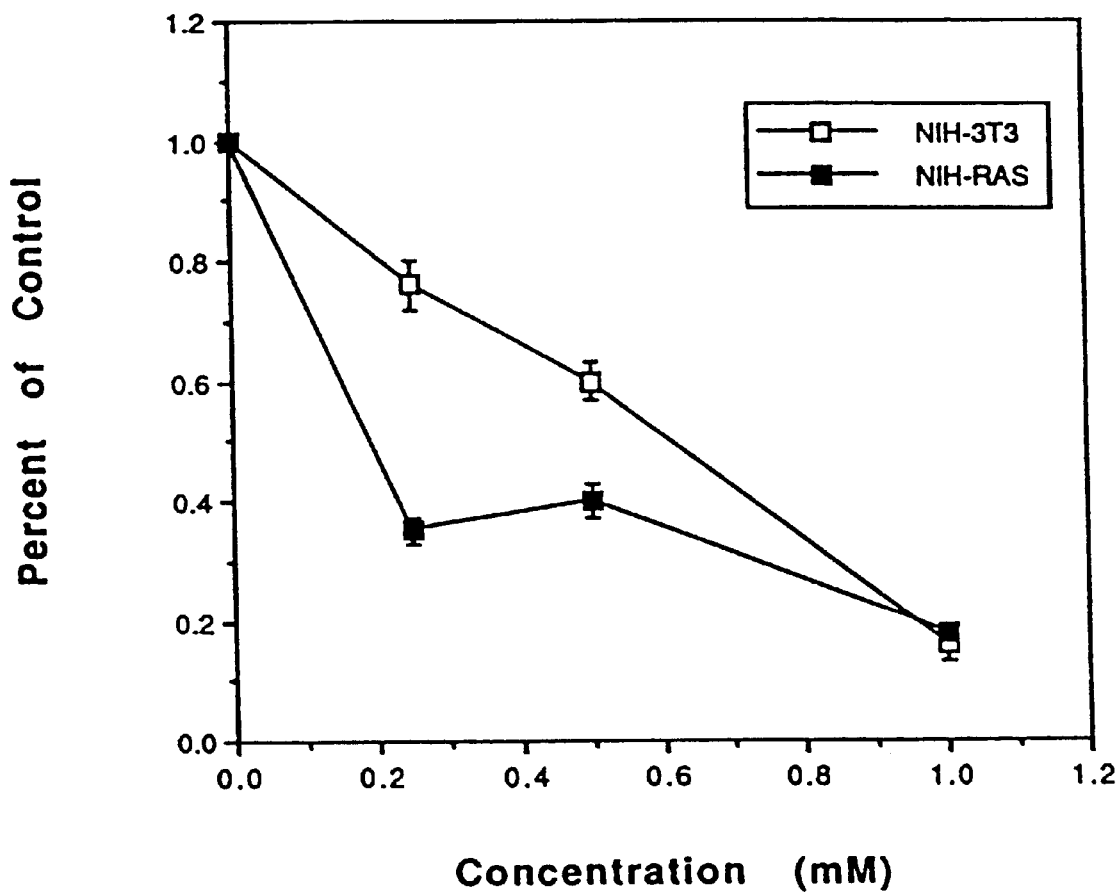
FIG. 4 shows cytotoxicity of inventive compound no. 1559 on NIH-3T3 cells and their Ras transformed counterpart, NIH-3T3 Ras cells. The cells were treated with various concentrations of compound no. 1559 and later stained for cell viability with a fluorescent stain. Compound no. 1559 is cytotoxic at higher concentrations, and thus shows anti-tumor activity.
Figure 5B:
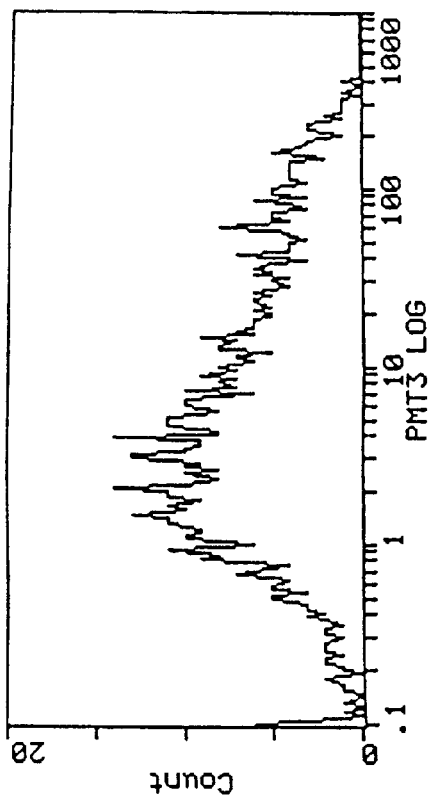
FIG. 5 shows the effect of compound no. 1559 to inhibit cell surface expression of VCAM in human umbilical vein endothelial cells (HUVEC).
Figure 5D:
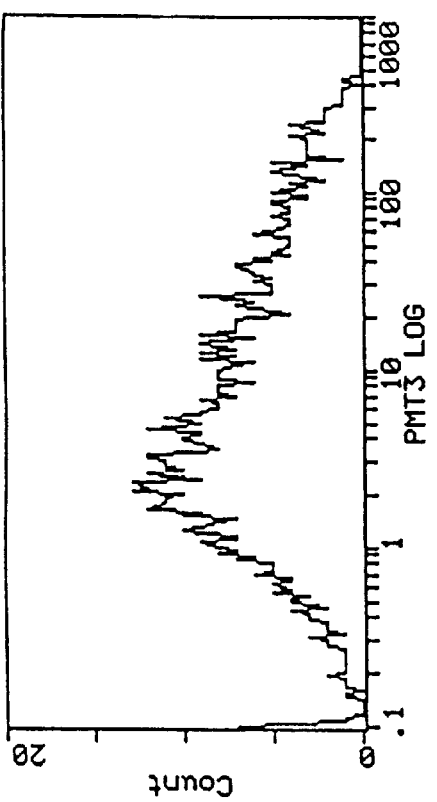
Figure 5A:
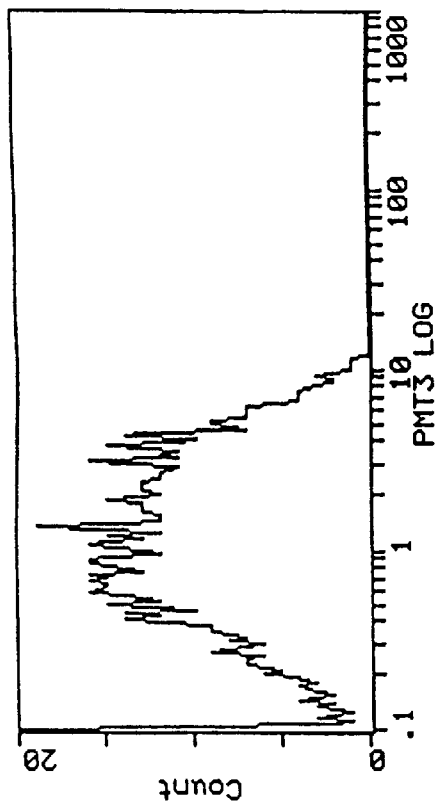
Figure 5C:
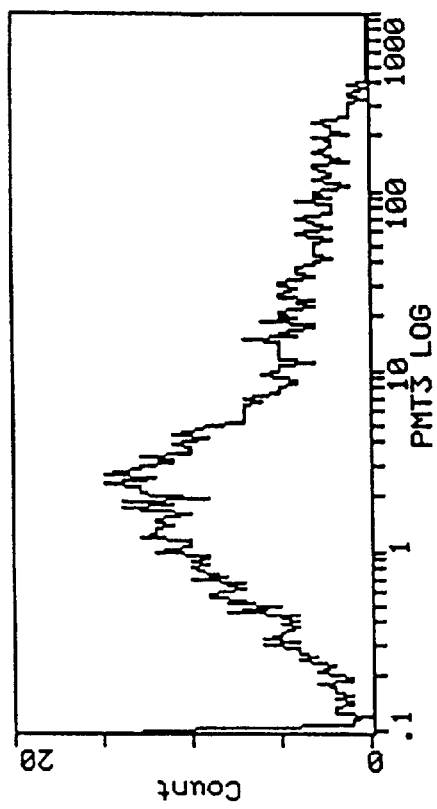

This example provides data from an experiment measuring compound no. 1559 cytotoxicity on NIH-3T3 cells and their Ras transformed counterpart, NIH-3T3 Ras cells. The cells were treated with various concentrations of compound no. 1559 and later stained for cell viability with a fluorescence stain (BCECF) and analyzed using a Milipore fluorescence plate reader. As shown in FIG. 4, compound no. 1559 is cytotoxic at higher concentrations, and thus shows antitumor activity.

Example 5

This example illustrates the effect of compound no. 1559 on inhibiting cell surface expression of VCAM in human umbilical vein endothelial cells (HUVEC). The HUVEC cells were stimulated with 20 ng/ml TNF- for 20 hours and then stained for immunofluorescence using a monoclonal antibody recognizing VCAM, followed by a goat anti-mouse antibody conjugated to phycoerythrin. The cells were analyzed for antibody binding using flow cytometry. FIG. 5 shows the flow cytometric frequency histograms plotting cell number versus relative fluorescence intensity. The top left histogram is non-TNF induced expression of VCAM (% of cells in gate A is 0.4%). The top right shows cells treated with TNF (% of cells in gate B is 34.5%). The lower left shows cells treated with compound no. 1559 (0.25 mM), one hour prior to TNF addition (% of cells in gate C is 24%). In the lower left, cells treated have been treated with PTX for comparison (% of cells in gate D is 36.8%).

Example 6

Figure 6:
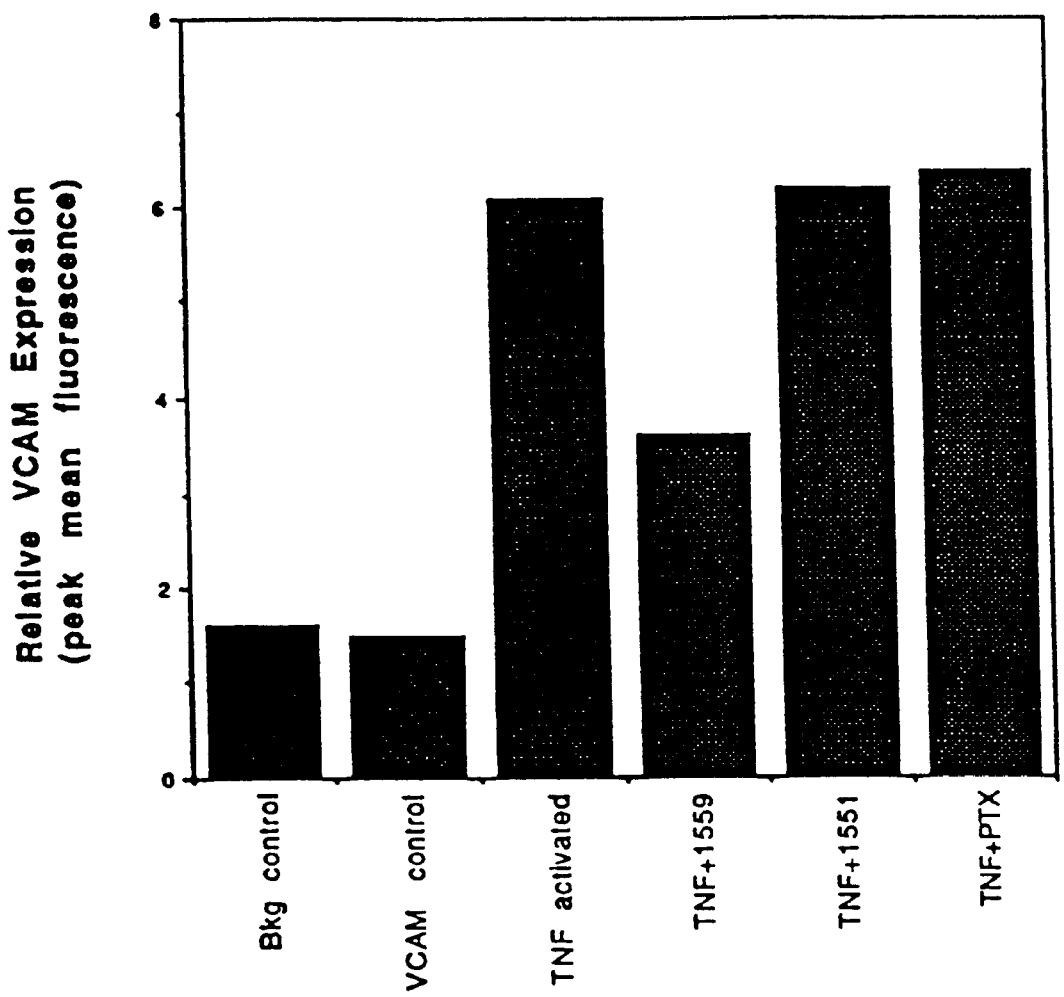
FIG. 6 shows mean fluorescence intensity of cells analyzed by flow cytometry, illustrating the effect of inventive compound no. 1559 on this cell line.

This example illustrates the effect of compound no. 1559 on inhibiting cell surface expression of VCAM in HUVEC cells. The cells were stimulated with TNF- (20 ng/ml) for 20 hours and then stained for immunofluorescence using a monoclonal antibody recognizing VCAM, followed by a goat anti-mouse antibody conjugated to phycoerythrin. The cells were analyzed for antibody binding using flow cytometry. FIG. 6 shows an analysis of mean fluorescence intensity of cells analyzed by flow cytometry. The mean fluorescence levels were decreased by compound no. 1559 treatment (1.7 fold decrease) when compared with control levels (TNF treatment, no drug).

Example 7

This example illustrates a comparison of MLR (mixed lymphocyte reaction) data for inventive comopounds of varying chain lengths to show a comparison of biological activity as a function of chain length (the number of carbon atoms between the hydroxyl carbon and the core moiety. A mixed lymphocyte reaction was run with a series of inventive compounds and other compounds. IC50 values for each compound tested was determined and the results listed in Table I below:

TABLE I

| Cpnd no. | Chain Length | Mean IC50 (M) | Formula II | Alcohol type |
|---|---|---|---|---|
| 1551 | 9 | 120 | Y | secondary |
| 1559 | 10 | 150 | Y | primary |
| 1561 | 9 | 185 | Y | diol |
| 1564 | 10 | 210 | Y | diol |
| 1501 | 6 | >500 | N | primary |
| 1502 | 6 | >500 | N | diol |
| 1536 | 8 | 250 | N | secondary |
| 1538 | 8 | >500 | N | diol |
| 1540 | 3 | >500 | N | diol |
| 1542 | 5 | >500 | N | secondary |
| 1545 | 7 | 300 | N | primary |
| 1546 | 8 | 320 | N | primary |
| 1556 | 6 | >500 | N | primary |

Accordingly, these data show the importance of chain length for immune modulating activity in the MLR assay.

Example 8

Figure 7A:
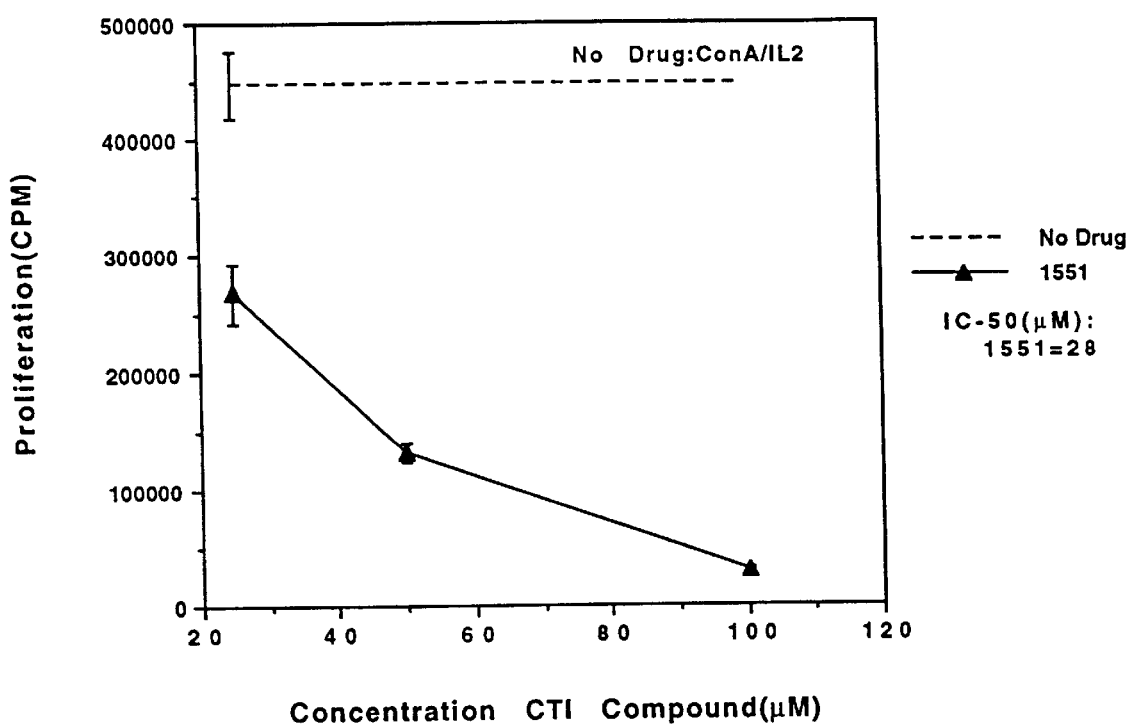
FIGS. 7A and 7B are drug dose response curves for compounds nos. 1551 and 1564 in an assay for murine thymocyte proliferation, co-stimulated by Concanavalin A (ConA) and interleukin-2 alpha (IL-2).
Figure 7B:
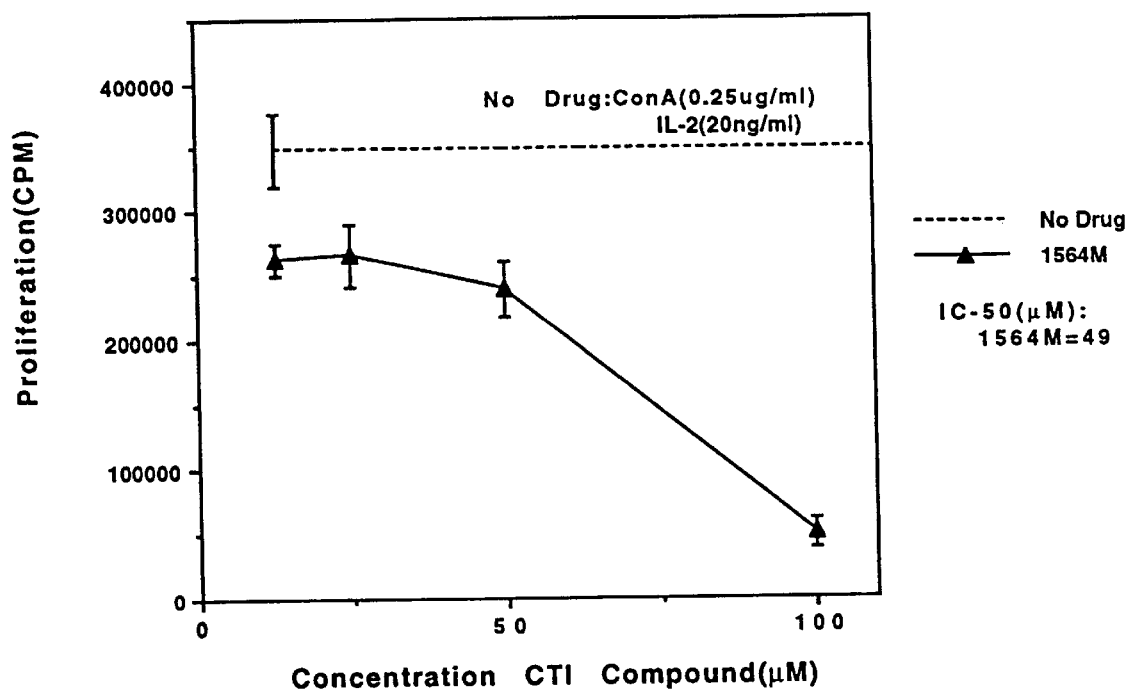

This example illustrates dose response curves used to generate 50% inhibition concentration (IC50) of inventive compounds nos. 1551 and 1564 for murine thymocyte proliferation, co-stimulated by Concanavalin A (ConA) and interleukin-2 alpha (IL-2). ConA, used to activate CD3, along with IL-2 co-stimulation, induces T-cell proliferation and differentiation. Thymuses, obtained from normal, female Balb/C mice, were dissociated and plated into 96-well plates at a density of $2 \times 10^5$ cells/well. ConA (0.25 mg/ml) and IL-2 (15 U/ml) were added to the wells. The cells were incubated for 4 days at 37° C. On day 4, the cells were pulsed with tritiated thymidine and incubated for an additional 4 hours. The amount of tritiated thymidine dye incorporated by the harvested cells was determined in a liquid scintillation counter. Drug doses (shown in FIGS. 7A and 7B) were added two hours prior to ConA and IL-2 activation. Background counts were less than 200 cpm. Both the inventive compounds inhibit thymocyte proliferation and activation and reported IC50 values for compounds nos. 1551 and 1564 are 28 and 49 $\mu$M.

Example 9

This example illustrates inhibitive and cytotoxic effects of inventive compounds nos. 2556 and 3504 on Balb/3T3 cell proliferation in response to PDGF-BB stimulation.

Figure 8A:
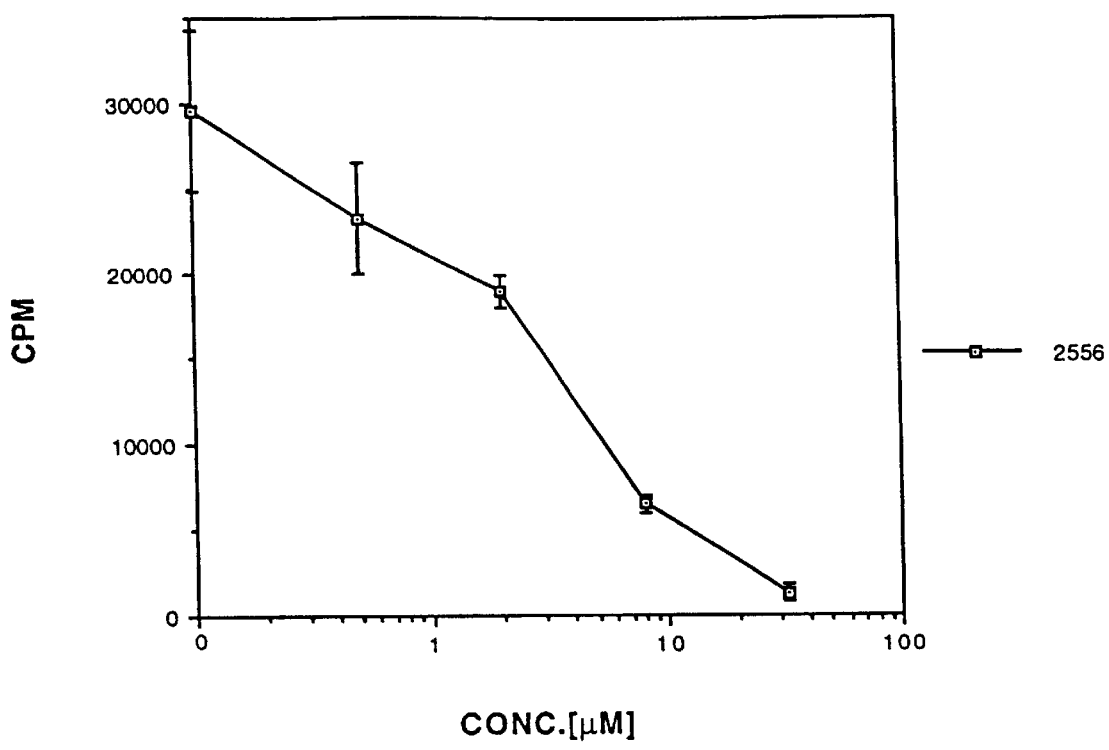
FIGS. 8A and 8B report inhibition activity and cytotoxicity data, respectively, for inventive compound no. 2556 in a Balb/3T3, PDGF-induced proliferation assay.
Figure 8B:
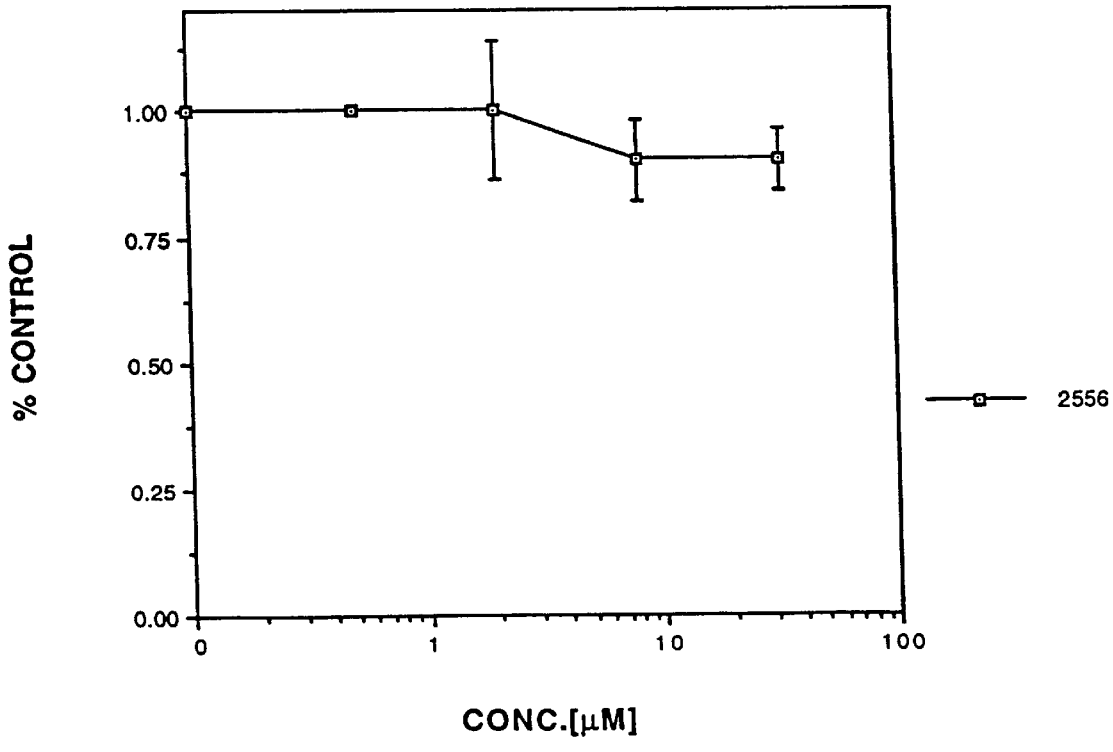
Figure 9A:
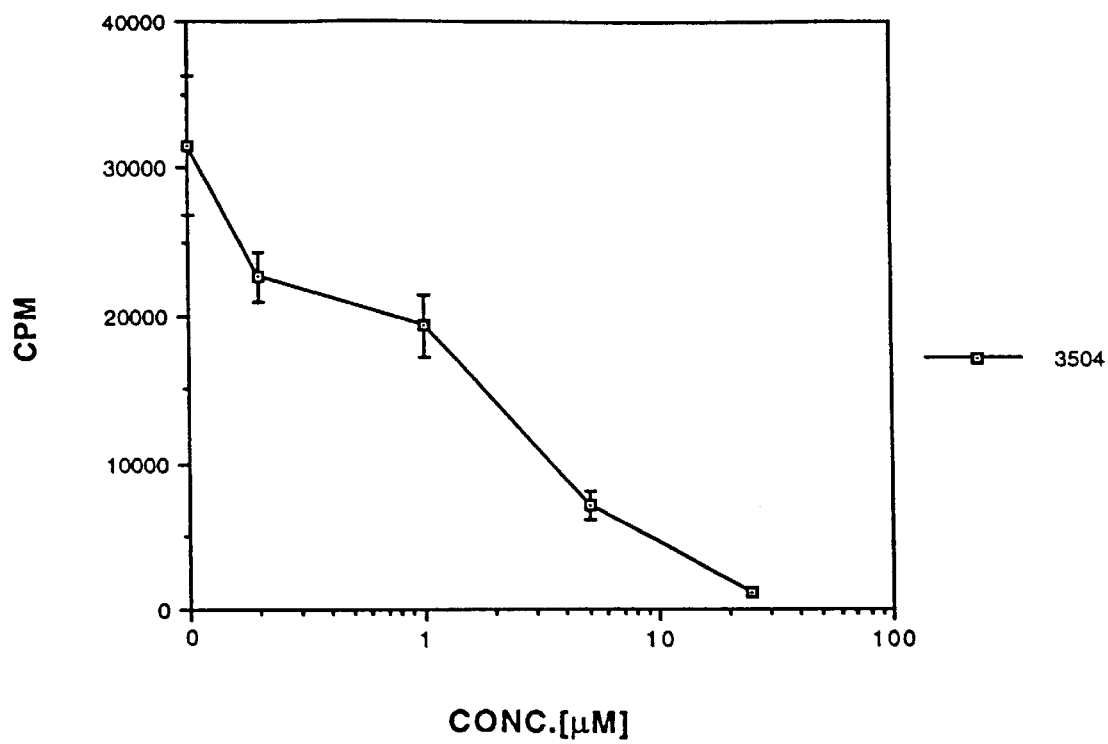
FIGS. 9A and 9B report inhibition activity and cytotoxicity data, respectively, for compounds nos. 2556 and 3504 in a Balb/3T3, PDGF-induced proliferation assay.
Figure 9B:
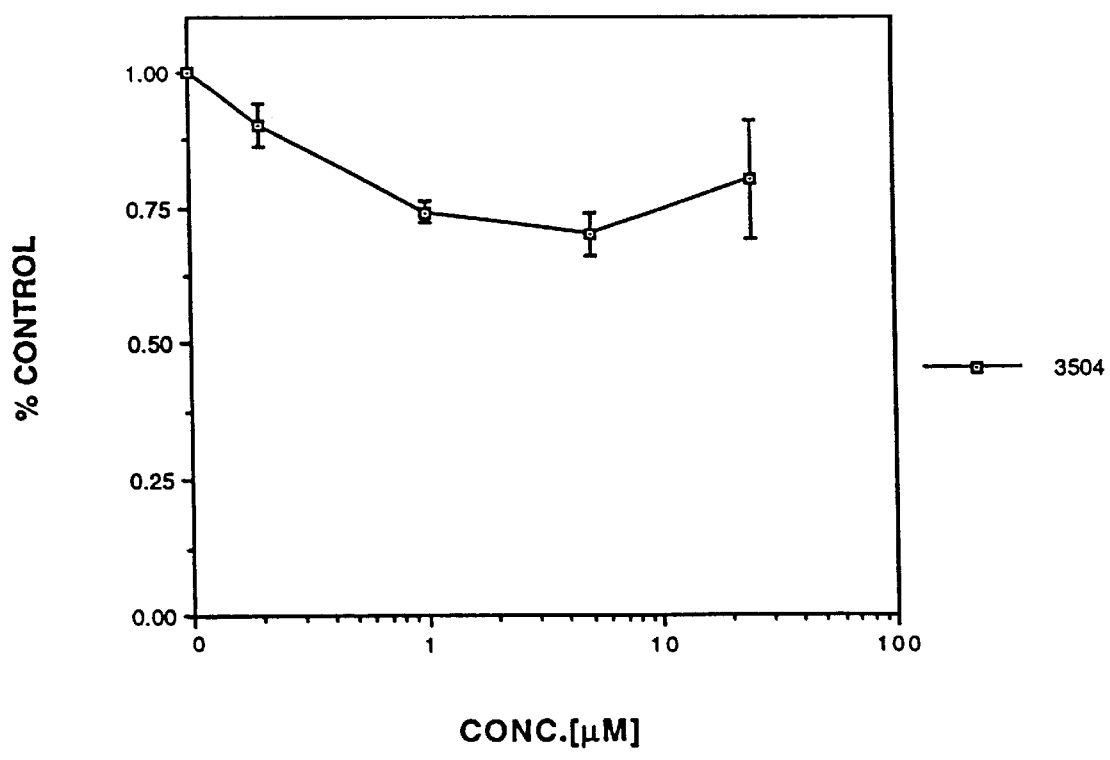

The inventive compounds possess inhibitory effects on PDGF-induced proliferation of Balb/3T3 cells. Balb/3T3 cells respond vigorously to PDGF stimulation, and are useful in vitro models for further study of PDGF-induced proliferation. Disregulated PDGF-proliferative response has been linked to a variety of diseases, including, e.g., restenosis, atherosclerosis, fibrosis, and tumor cell angiogenesis. Cells were plated in low serum-containing medium for 24 hours prior to stimulation with various concentrations (as reported in FIGS. 8A and 9A) of inventive compounds nos.2556 and 3504 (FIGS. 8A and 9A, respectively). PDGF-BB was added at a constant concentration in each assay. Tritiated thymidine was added and cells harvested for scintillation counting 24 hours later. FIGS. 8A and 9A are dose response curves from this assay for compound nos. 2556 and 3504, respectively. FIGS. 8B and 9B report cytotoxicity results for compounds nos. 2556 and 3504 in the Balb/3T3 cell line. Both inventive compounds tested inhibited PDGF-induced proliferation in Balb/3T3 cells.

Example 10

This example illustrates the assay used to determine the effect of compounds of this invention in suppressing Th1 differentiation in vitro by blocking IL-12 signaling. Compounds are tested in an IL-12 dependent in vitro T-helper cell differentiation assay as described in LeGross et al., *J. Exp. Med.*, 172:921–929 (1990). Recombinant IL-12 is used to induce Th1 differentiation. Splenic T cells are purified utilizing the antibodies RA3-3A1/6.1 (anti-B220), J11d and MAR8.5 (anti-rat kappa chain) to deplete the B cells via complement mediated toxicity following the procedure set forth in Klaus et al., *J. Immunol.*, 149:1867–1875 (1992). Splenic T cells are stimulated at $5 \times 10^5$/ml with insoluble anti-CD3 alone (145-2C11, Pharmingen, San Diego, Calif.), or anti-CD3 and 5 U/ml IL-12, with and without each inventive compound. After seven days, equal numbers of viable cells are restimulated for 24 hours with anti-CD3 without the inventive compounds, and the supernatants are collected and assayed for IFN-γ production. IFN-γ and IL-4 levels are measured by Intertest kits from Genzyme specific for IFN-γ and IL-4.

Th1 differentiation is induced by culturing anti-CD3 stimulated T cells in the presence of exogenous IL-12. Under these conditions, Th1 differentiation is consistently enhanced as compared to T cells stimulated with anti-CD3 alone. Using this assay, it was observed that the presence of CT 1536 (i.e., 1-(7-Hydroxyoctyl)-3,7-dimethylxanthine) during T cell activation inhibited Th1 differentiation that had been enhanced by the addition of exogenous IL-12. Neither the viability or recovery of T cells after one week of culture in the presence of the compound.

Example 11

The ability of IL-12 to induce generation of Th1 cells is aided by IFN-γ, a cytokine which is known to be induced by IL-12 itself. Compounds of the invention are tested for their effects on IFN-γ production induced by IL-12 in an interferon gamma (IFN-γ) induction assay essentially as described in Kobayashi, M, et al., "Identification and Purification of Natural Killer Cell Stimulatory Factor (NKSF), A Cytokine with Multiple Biologic Effects on Human Lymphocytes," *J. Exp. Med U*, 170:827–845 (at 829, 830 and 836) (1989). See also, Wolf, S., et al., "Interleukin 12: A Key Modulator of Immune Function," *Stem Cells*, 12:154–168 (1994) and Trinchieri, supra.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

All of the publications, patent applications and patents cited in this application are herein incorporated by reference in their entirety to the same extent as if each individual publication, patent application or patent was specifically and individually indicated to be incorporated by reference in its entirety.

What is claimed is:

1. A method for modulating the response of a target cell to a stimulus, which method comprises:
(a) contacting said cell with an effective amount of a compound of the formula, $(R)_j$—(CORE MOIETY), including resolved enantiomers, diastereomers, hydrates, salts, solvates or mixtures thereof, wherein j is an integer from one to three, the core moiety is a xanthinyl bicyclic ring, R is selected from the group consisting of hydrogen, halogen, hydroxyl, amino, substituted or unsubstituted benzyl, $C_{1-6}$ alkyl or $C_{1-6}$ alkenyl, and at least one R has the formula I:

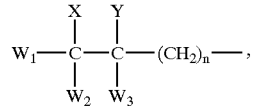

wherein n is an integer from 1 to 20, at least one of X or Y is —OH, another of X or Y, which is not —OH, being selected from H, $CH_3$, $CH_3$—$CH_2$—, $CH_3$—$(CH_2)_2$—, or $(CH_3)_2$—$CH_2$—, and each $W_1$, $W_2$, and $W_3$ is independently selected from H, $CH_3$, $CH_3$—$CH_2$—, $CH_3$—$(CH_2)_2$—, or $(CH_3)_2$—$CH_2$—, said X, Y, $W_1$, $W_2$ or $W_3$ alkyl groups being unsubstituted or substituted by a hydroxyl, halo or dimethylamino group; and (b) determining that the response of the target cell is thereby modulated; wherein: said stimulus is capable of elevating the cellular level of non-arachidonate phosphatidic acid (PA) and diacylglycerol (DAG) derived therefrom, said compound is provided in an amount effective to reduce the elevated levels of PA and DAG that result from said stimulus, and the reduction in elevated levels is equal to or greater than that produced by treating the cells with pentoxifylline (PTX) at a concentration of 0.5 mmol.

2. The method of claim 1, wherein n in said compound is an integer of 4 to 20.

3. The method of claim 1, wherein n in said compound is an integer of 8 to 20.

4. The method of claim 1, wherein n in said compound is an integer of 6 to 12.

5. The method of claim 1, wherein n in said compound is an integer of 9 to 15.

6. A method for inhibiting a cellular process or activity mediated by IL-12 signalling comprising the steps of:
(a) contacting IL-12 responsive target cells with a compound of the formula, $(R)_j$—(CORE MOIETY), including resolved enantiomers, diastereomers, hydrates, salts, solvates or mixtures thereof, wherein j is an integer from one to three, the core moiety is a xanthinyl bicyclic ring, R is selected from the group consisting of hydrogen, halogen, hydroxyl, amino, substituted or unsubstituted benzyl, $C_{1-6}$ alkyl or $C_{1-6}$ alkenyl, and at least one R has the formula I:

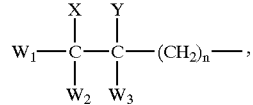

wherein n is an integer from 1 to 20, at least one of X or Y is —OH, another of X or Y, which is not —OH, being selected from H, $CH_3$, $CH_3$—$CH_2$—, $CH_3$—$(CH_2)_2$—, or $(CH_3)_2$—$CH_2$—, and each $W_1$, $W_2$, and $W_3$ is independently selected from H, $CH_3$, $CH_3$—$CH_2$—, $CH_3$—$(CH_2)_2$—, or $(CH_3)_2$—$CH_2$—, said X, Y, $W_1$, $W_2$ or $W_3$ alkyl groups being unsubstituted or substituted by a hydroxyl, halo or dimethylamino group; and
(b) determining that the response of the target cell is thereby modulated.

7. The method of claim 6, wherein the zanthinyl core moiety has the following formula II:

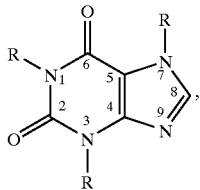

wherein R is the same as defined in claim 8.

8. The method of claim 7, werein at least on R of Formula I is bonded to the $N_1$ of said xanthinyl core moiety and n in said R is an integer of 3 to 7.

9. The method of claim 8, wherein said compound has the structure,

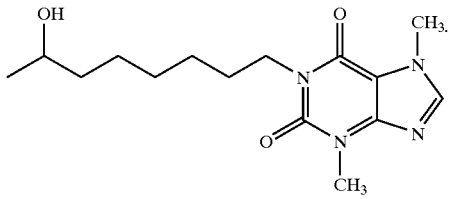

10. The method of claim 6, wherein said cellular activity is the secretion of proinflammatory cytokines.

11. The method of claim 6, wherein said cellular process is the differentiation of naïve T cells into Th1 cells.

12. A method for treating a Th1 cell-mediated inflammatory response in a mannal in need of such treatment, the method comprising:
administering to the mannal a therapeutically effective amount of a compunt of the formula, $(R)_j$—(CORE MOIETY), including resolved enantiomers, diastereomers, hydrates, salts, solvates or mixtures thereof, wherein j is an integer from one to three, the core moiety is a xanthinyl bicyclic ring, R is selected from the group consisting of hydrogen, halogen, hydroxyl, amino, substituted or unsubstituted benzyl, $C_{1-6}$ alkyl or $C_{1-6}$ alkenyl, and at least one R has the formula I:

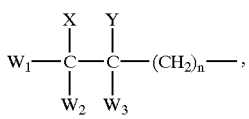

wherein n is an integer from 1 to 20, at least one of X or Y is —OH, another of X or Y, which is not —OH, being selected from H, $CH_3$, $CH_3$—$CH_2$—, $CH_3$—$(CH_2)_2$—, or $(CH_3)_2$—$CH_2$—, and each $W_1$, $W_2$, and $W_3$ is independently selected from H, $CH_3$, $CH_3$—$CH_2$—, $CH_3$—$(CH_2)_2$—, or $(CH_3)_2$—$CH_2$—, said X, Y, $W_1$, $W_2$ or $W_3$ alkyl groups being unsubstituted or substituted by a hydroxyl, halo or dimethylamino group; and
wherein said compound is capable of inhibiting and IL-12 mediated celluar process or activity, thereby inhibiting the inflammatory response.

13. The method of claim 12, wherein the xanthinyl core moiety has the following formula II:

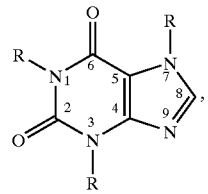

wherein R is the same as defined in claim 12.

14. The method of claim 13, wherein at least one R of Formula I is bonded to the $N_1$ of said xanthinyl core moiety and n in said R is an integer of 3 to 7.

15. The method of claim 14, wherein said compound has the structure,

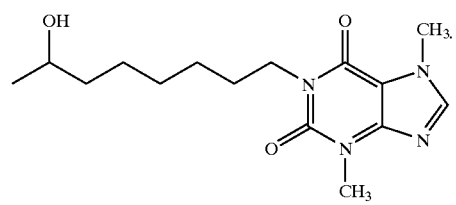

16. The method of claim 12, wherein the inflammatory response is associated with a disease or condition selected from the group consisting of chronic inflammatory disease, chronic intestinal inflammation, arthritis, psoriasis, asthma and autoimmune disorders.

17. The method of claim 1, wherein said compound is 1-(7-hydroxyoctyl)-3,7-dimethylxanthine.

18. The method of claim 1, wherein the xanthinyl core moiety having the following formula II:

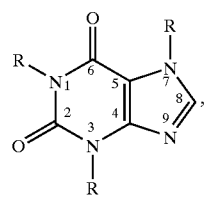

wherein R is selected from the group consisting of hydrogen, halogen, hydroxyl, amino, substituted or unsubstituted benzyl, $C_{1-6}$ alkyl or $C_{1-6}$ alkenyl, and at least one R has the formula I:

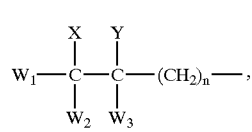

wherein n is an integer from 1 to 20, at least one of X or Y is —OH, another of X or Y, which is not —OH, being selected from H, $CH_3$, $CH_3$—$CH_2$—, $CH_3$—$(CH_2)_2$—, or $(CH_3)_2$—$CH_2$—, and each $W_1$, $W_2$, and $W_3$ is independently selected from H, $CH_3$, $CH_3$—$CH_2$—, $CH_3$—$(CH_2)_2$—, or $(CH_3)_2$—$CH_2$—, said X, Y, $W_1$, $W_2$ or $W_3$ alkyl groups being unsubstituted or substituted by a hydroxyl, halo or dimethylamino group.

* * * * *